United States Patent
Ford et al.

(10) Patent No.: US 8,956,373 B2
(45) Date of Patent: *Feb. 17, 2015

(54) IMPLANTABLE PROSTHESIS

(75) Inventors: Steven Palmer Ford, Riverside, RI (US); Donna Schultz Torres, Attleboro, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/842,629

(22) Filed: Jul. 23, 2010

(65) Prior Publication Data

US 2010/0286716 A1    Nov. 11, 2010

Related U.S. Application Data

(63) Continuation of application No. 11/508,447, filed on Aug. 23, 2006, now Pat. No. 7,785,334, which is a continuation of application No. 10/212,006, filed on Aug. 2, 2002, now Pat. No. 7,101,381.

(51) Int. Cl.
*A61B 17/08* (2006.01)
*A61F 2/02* (2006.01)
(Continued)

(52) U.S. Cl.
CPC .......... *A61B 17/0057* (2013.01); *A61F 2/0063* (2013.01); *A61B 17/00234* (2013.01); *A61B 2017/00637* (2013.01); *A61B 2017/00659* (2013.01); *A61F 2250/0051* (2013.01)
USPC ...................... 606/151; 623/11.11; 623/23.72

(58) Field of Classification Search
USPC .......... 606/151, 192; 600/29, 30, 37; 602/44, 602/67, 76, 70; 128/95.1, 99.1; 623/23.72, 623/23.76, 11.11
See application file for complete search history.

(56) References Cited

U.S. PATENT DOCUMENTS

| 2,143,910 A | 1/1939 | Didusch |
|---|---|---|
| 2,671,444 A | 3/1954 | Pease, Jr. |

(Continued)

FOREIGN PATENT DOCUMENTS

| CA | 2 114 282 A1 | 7/1994 |
|---|---|---|
| EP | 0 362 113 A1 | 4/1990 |

(Continued)

OTHER PUBLICATIONS

Kugel, Robert D., "Minimally Invasive Repair of Groin and Ventral Hernias Using a Self-Expanding Mesh Patch," *Surgical Technology International X*, Sep. 2002, pp. 81-87.

(Continued)

*Primary Examiner* — Julian W Woo
(74) *Attorney, Agent, or Firm* — Wolf, Greenfield & Sacks, P.C.

(57) ABSTRACT

An implantable prosthesis for repairing an anatomical defect, such as a tissue or muscle wall hernia, including an umbilical hernia, and for preventing the occurrence of a hernia at a small opening or weakness in a tissue or muscle wall, such as at a puncture tract opening remaining after completion of a laparoscopic procedure. The prosthesis includes a patch for covering or extending across the opening or weakness. At least one tether, such as a strap, extends from the patch and may be manipulated to position and/or to secure the patch relative to the opening or weakness in the tissue or muscle wall. The tether may be configured to extend through the defect and outside a patient's body for positioning and/or manipulating the patch from a location outside the body. A support member may be arranged in or on the patch to help deploy the patch at the surgical site and/or help inhibit collapse or buckling of the patch.

56 Claims, 11 Drawing Sheets

(51) Int. Cl.
  *A61B 17/00* (2006.01)
  *A61F 2/00* (2006.01)

(56) References Cited

U.S. PATENT DOCUMENTS

| | | | |
|---|---|---|---|
| 3,054,406 A | 9/1962 | Usher |
| 3,124,136 A | 3/1964 | Usher |
| 3,416,524 A | 12/1968 | Meier |
| 3,874,388 A | 4/1975 | King et al. |
| 4,007,743 A | 2/1977 | Blake |
| 4,054,316 A | 10/1977 | DeLong |
| 4,452,245 A | 6/1984 | Usher |
| 4,478,665 A | 10/1984 | Hubis |
| 4,482,516 A | 11/1984 | Bowman et al. |
| 4,561,434 A | 12/1985 | Taylor |
| 4,595,007 A | 6/1986 | Mericle |
| 4,598,011 A | 7/1986 | Bowman |
| 4,633,873 A | 1/1987 | Dumican et al. |
| 4,655,221 A | 4/1987 | Devereux |
| 4,693,720 A | 9/1987 | Scharnberg et al. |
| 4,710,192 A | 12/1987 | Liotta et al. |
| 4,769,038 A | 9/1988 | Bendavid et al. |
| 4,796,603 A | 1/1989 | Dahlke et al. |
| 4,836,204 A | 6/1989 | Landymore et al. |
| 4,854,316 A | 8/1989 | Davis |
| 4,865,026 A | 9/1989 | Barrett |
| 4,917,089 A | 4/1990 | Sideris |
| 4,923,464 A | 5/1990 | DiPisa, Jr. |
| 4,942,875 A | 7/1990 | Hlavacek et al. |
| 4,955,907 A | 9/1990 | Ledergerber |
| 5,002,572 A | 3/1991 | Picha |
| 5,006,106 A | 4/1991 | Angelchik |
| 5,053,047 A | 10/1991 | Yoon |
| 5,059,205 A | 10/1991 | El-Nounou et al. |
| 5,092,884 A | 3/1992 | Devereux et al. |
| 5,108,420 A | 4/1992 | Marks |
| 5,116,357 A | 5/1992 | Eberbach |
| 5,122,155 A | 6/1992 | Eberbach |
| 5,141,515 A | 8/1992 | Eberbach |
| 5,147,374 A | 9/1992 | Fernandez |
| 5,147,384 A | 9/1992 | La Rocca |
| 5,147,387 A | 9/1992 | Jansen et al. |
| 5,171,259 A | 12/1992 | Inoue |
| 5,176,692 A | 1/1993 | Wilk et al. |
| 5,192,301 A | 3/1993 | Kamiya et al. |
| 5,192,302 A | 3/1993 | Kensey et al. |
| 5,195,542 A | 3/1993 | Gazielly et al. |
| 5,201,745 A | 4/1993 | Tayot et al. |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |
| 5,263,969 A | 11/1993 | Phillips |
| 5,269,774 A | 12/1993 | Gray |
| 5,282,856 A | 2/1994 | Ledergerber |
| 5,290,217 A | 3/1994 | Campos |
| 5,292,328 A | 3/1994 | Hain et al. |
| 5,304,187 A | 4/1994 | Green et al. |
| 5,334,217 A | 8/1994 | Das |
| 5,350,399 A | 9/1994 | Erlebacher et al. |
| 5,356,432 A | 10/1994 | Rutkow et al. |
| 5,366,460 A | 11/1994 | Eberbach |
| 5,368,602 A | 11/1994 | de la Torre |
| 5,368,606 A | 11/1994 | Marlow et al. |
| 5,370,650 A | 12/1994 | Tovey et al. |
| 5,379,754 A | 1/1995 | Tovey et al. |
| 5,380,277 A | 1/1995 | Phillips |
| 5,383,477 A | 1/1995 | DeMatteis |
| 5,397,331 A | 3/1995 | Himpens et al. |
| 5,397,332 A | 3/1995 | Kammerer et al. |
| 5,405,360 A | 4/1995 | Tovey |
| 5,425,740 A | 6/1995 | Hutchinson, Jr. |
| 5,425,744 A | 6/1995 | Fagan et al. |
| 5,433,996 A | 7/1995 | Kranzler et al. |
| 5,450,860 A | 9/1995 | O'Connor |
| 5,451,235 A | 9/1995 | Lock et al. |
| 5,456,720 A | 10/1995 | Schultz et al. |
| 5,458,636 A | 10/1995 | Brancato |
| 5,464,403 A | 11/1995 | Kieturakis et al. |
| 5,480,436 A | 1/1996 | Bakker et al. |
| 5,496,345 A * | 3/1996 | Kieturakis et al. ............ 606/192 |
| 5,503,623 A | 4/1996 | Tilton, Jr. |
| 5,507,811 A | 4/1996 | Koike et al. |
| 5,508,036 A | 4/1996 | Bakker et al. |
| 5,531,759 A | 7/1996 | Kensey et al. |
| 5,545,178 A | 8/1996 | Kensey et al. |
| 5,569,273 A | 10/1996 | Titone et al. |
| 5,593,441 A | 1/1997 | Lichtenstein et al. |
| 5,634,931 A | 6/1997 | Kugel |
| 5,634,944 A | 6/1997 | Magram |
| 5,653,755 A | 8/1997 | Ledergerber |
| 5,681,342 A | 10/1997 | Benchetrit |
| 5,686,090 A | 11/1997 | Schilder et al. |
| 5,695,525 A | 12/1997 | Mulhauser et al. |
| 5,697,978 A | 12/1997 | Sgro |
| 5,702,416 A | 12/1997 | Kieturakis et al. |
| 5,709,707 A | 1/1998 | Lock et al. |
| 5,713,947 A | 2/1998 | Davidson |
| 5,716,408 A | 2/1998 | Eldridge et al. |
| 5,716,409 A | 2/1998 | Debbas |
| 5,723,010 A | 3/1998 | Yui et al. |
| 5,725,577 A | 3/1998 | Saxon |
| 5,728,157 A | 3/1998 | Prescott |
| 5,733,294 A | 3/1998 | Forber et al. |
| 5,733,337 A | 3/1998 | Carr, Jr. et al. |
| 5,741,297 A | 4/1998 | Simon |
| 5,743,917 A | 4/1998 | Saxon |
| 5,755,769 A | 5/1998 | Richard et al. |
| 5,766,246 A | 6/1998 | Mulhauser et al. |
| 5,766,248 A | 6/1998 | Donovan |
| 5,769,864 A | 6/1998 | Kugel |
| 5,772,680 A | 6/1998 | Kieturakis et al. |
| 5,782,913 A | 7/1998 | Schindler et al. |
| 5,785,713 A | 7/1998 | Jobe |
| 5,813,975 A | 9/1998 | Valenti |
| 5,814,057 A | 9/1998 | Oi et al. |
| 5,824,082 A | 10/1998 | Brown |
| 5,827,325 A | 10/1998 | Landgrebe et al. |
| 5,836,961 A | 11/1998 | Kieturakis et al. |
| 5,840,083 A | 11/1998 | Braach-Maksvytis |
| 5,861,036 A | 1/1999 | Godin |
| 5,876,446 A | 3/1999 | Agrawal et al. |
| 5,876,451 A | 3/1999 | Yui et al. |
| 5,879,366 A | 3/1999 | Shaw et al. |
| 5,897,590 A | 4/1999 | Donovan |
| 5,910,168 A | 6/1999 | Myers et al. |
| 5,916,225 A | 6/1999 | Kugel |
| 5,919,232 A | 7/1999 | Chaffringeon et al. |
| 5,919,233 A | 7/1999 | Knopf et al. |
| 5,922,025 A | 7/1999 | Hubbard |
| 5,922,026 A | 7/1999 | Chin |
| 5,948,020 A | 9/1999 | Yoon et al. |
| 5,954,767 A | 9/1999 | Pajotin et al. |
| 5,972,022 A | 10/1999 | Huxel |
| 6,004,333 A | 12/1999 | Sheffield et al. |
| 6,042,534 A | 3/2000 | Gellman et al. |
| 6,066,776 A | 5/2000 | Goodwin et al. |
| 6,080,182 A | 6/2000 | Shaw et al. |
| 6,113,623 A | 9/2000 | Sgro |
| 6,113,641 A | 9/2000 | Leroy et al. |
| 6,120,539 A | 9/2000 | Eldridge et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,180,848 B1 | 1/2001 | Flament et al. |
| 6,193,731 B1 | 2/2001 | Oppelt et al. |
| 6,197,036 B1 | 3/2001 | Tripp et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,267,772 B1 | 7/2001 | Mulhauser et al. |
| 6,270,530 B1 | 8/2001 | Eldridge et al. |
| 6,280,453 B1 | 8/2001 | Kugel et al. |

(56) References Cited

U.S. PATENT DOCUMENTS

| | | | |
|---|---|---|---|
| 6,287,316 | B1 | 9/2001 | Agarwal et al. |
| 6,290,708 | B1 | 9/2001 | Kugel et al. |
| 6,319,264 | B1 | 11/2001 | Tormala et al. |
| 6,383,201 | B1 | 5/2002 | Dong |
| 6,551,356 | B2 | 4/2003 | Rousseau |
| 6,669,735 | B1 | 12/2003 | Pelissier et al. |
| 6,790,213 | B2 | 9/2004 | Cherok |
| 6,926,723 | B1 | 8/2005 | Mulhauser |
| 7,101,381 | B2 | 9/2006 | Ford et al. |
| 7,785,334 | B2 * | 8/2010 | Ford et al. ............... 606/151 |
| 7,806,905 | B2 | 10/2010 | Ford et al. |
| 2001/0027347 | A1 | 10/2001 | Rousseau |
| 2002/0013590 | A1 | 1/2002 | Therin et al. |
| 2002/0028980 | A1 | 3/2002 | Thierfelder et al. |
| 2002/0052654 | A1 | 5/2002 | Darois et al. |
| 2002/0055701 | A1 | 5/2002 | Fischell et al. |
| 2002/0077652 | A1 | 6/2002 | Kieturakis et al. |
| 2002/0103494 | A1 | 8/2002 | Pacey |
| 2013/0226232 | A1 | 8/2013 | Dumanian et al. |

FOREIGN PATENT DOCUMENTS

| | | |
|---|---|---|
| EP | 0 474 887 A1 | 3/1992 |
| EP | 0 362 113 B1 | 4/1993 |
| EP | 0 655 222 A | 5/1995 |
| EP | 0 706 778 A1 | 4/1996 |
| EP | 0 888 756 A2 | 1/1999 |
| EP | 0 898 944 A2 | 3/1999 |
| EP | 0 898 944 A3 | 8/1999 |
| EP | 1 219 265 A | 7/2002 |
| EP | 1 524 951 B1 | 2/2012 |
| FR | 2735353 A1 | 12/1996 |
| FR | 2778554 A1 | 11/1999 |
| JP | 7-47090 A | 2/1995 |
| JP | 2001-353171 | 12/2001 |
| JP | 2002-209901 A | 7/2002 |
| JP | 2000-245756 A | 9/2009 |
| SU | 676285 A1 | 7/1979 |
| WO | WO 90/14796 A1 | 12/1990 |
| WO | WO 96/40307 A1 | 12/1996 |
| WO | WO 97/22310 A2 | 6/1997 |
| WO | WO 97/35533 A1 | 10/1997 |
| WO | WO 99/56664 A1 | 11/1999 |
| WO | WO 00/07520 A1 | 2/2000 |
| WO | 00/16822 A1 | 3/2000 |
| WO | WO 00/16822 | 3/2000 |
| WO | WO 00/42943 A1 | 7/2000 |
| WO | WO 01/08594 A1 | 2/2001 |
| WO | WO 02/22047 A1 | 3/2002 |
| WO | WO 03/073960 | 9/2003 |
| WO | WO 03/105727 | 12/2003 |

OTHER PUBLICATIONS

Grant, A.M., "Open Mesh Versus Non-Mesh Repair of Groin Hernia Meta-Analysis of Randomized Trials Leased on Individual Patient Data," *Hernia* ,2002, vol. 6, pp. 130-136.
European Office Action, mailed Aug. 19, 2008, for European Patent Application No. 03 738 891.5.
Translation of Notice of Reasons for Rejection for Japanese Patent Application No. 2004-525974, mailed Mar. 31, 2009.
Canadian Office Action, mailed Nov. 27, 2009, for Canadian Patent Application No. 2,494,111 (4 pages).
English translation of the Notice of Reasons for Rejection, mailed Sep. 2, 2011, for Japanese Patent Application No. 2009-226457 (4 pages).
English translation of the Notice of Reasons for Rejection, mailed Sep. 2, 2011, for Japanese Patent Application No. 2009-226461 (3 pages).
Extended European Search Report, dated Feb. 16, 2012, for European Application No. 10181775.7 (8 pages).
Extended European Search Report, dated Feb. 21, 2012, for European Application No. 10181809.4 (7 pages).
Extended European Search Report, dated Feb. 16, 2012, for European Application No. 10181840.9 (7 pages).
Ethicon, Inc., Notice of Opposition to a European Patent and Grounds of Opposition against EP 1 524 951 B1, filed on Nov. 1, 2012.
Atrium Medical Corporation, Notice of Opposition to a European Patent and Grounds of Opposition against EP 1 524 951 B1, filed on Nov. 2, 2012.
510(K) Summary of Safety and Effectiveness for the Composix E/X Mesh, Davol, Inc., FDA 510K approval Jan. 22, 2001.
510(K) Summary of Safety and Effectiveness for the Ventralex Patch, Davol, Inc., FDA 510K approval Jul. 16, 2002.
Bellón, Juan M., Evaluation of a New Composite Prosthesis (PL-PU99) for the Repair of Abdominal Wall Defects in Terms of Behavior at the Peritoneal Interface, World J. Surg., vol. 26, No. 6, pp. 661-666, Jun. 2002 (published online Mar. 1, 2002).
Bendavid, Robert, a Femoral "Umbrella" for Femoral Hernia Repair, Surgery, Gynecology & Obstetrics, vol. 165, pp. 153-156, Aug. 1987.
Bendavid, Robert, New Techniques in Hernia Repair, World J. Surgery, vol. 13, No. 5, pp. 522-531, Sep./Oct. 1989.
Greenawalt, Keith E., Evaluation of Sepramesh Biosurgical Composite in a Rabbit Hernia Repair Model, Journal of Surgical Research, vol. 94, No. 2, pp. 92-98, Dec. 2000.
Helfrich, Richard B., Abdominal Wall Hernia Repair: Use of the Gianturco-Helfrich-Eberbach Hernia Mesh, Journal of Laparoendoscopic Surgery, vol. 5, No. 2, pp. 91-95, 1995.
Bard Composix Kugel Hernia Patch, © 2001.
Kugel, Robert D. Minimally Invasive, Nonlaparoscopic, Preperitoneal, and Sutureless, Inguinal Herniorraphy, The American Journal of Surgery, vol. 178, pp. 298-302, 1999.
Lichtenstein, Irving L., Repair of Recurrent Ventral Hernias by an Internal "Binder", The American Journal of Surgery, vol. 132, pp. 121-125, Jul. 1976.
Moreno-Egea, Alfredo, Laparoscopic Repair of Ventral and Incisional Hernias Using a New Composite Mesh (Parietex), Surgical Laparoscopy, Endoscopy & Percutaneous Techniques, vol. 11, No. 2, pp. 103-106, 2001.
Affidavit of Christopher Butler, Dated Dec. 11, 2012.
Bard Composix Kugel Hernia Patch Website, dated Apr. 12, 2001, available at http://web.archive.org/web/20010412200712/http:/davol.com/kugcomp.htm (obtained via Internet Archive).
Communication mailed Feb. 6, 2013 for European application No. 10 181 775.7 (6 pages).
Communication mailed Feb. 8, 2013 for European application No. 10 181 840.9 (5 pages).
English translation of the Notice of Reasons for Rejection, mailed Apr. 9, 2013, for Japanese Patent Application No. 2012-000479 (3 pages).
Corrected Petition for Inter Partes Review of Claims 1-23 and 78-98 of U.S. Patent No. 7,785,334 under 35 U.S.C. § 312 and 37 C.F.R. § 42.104, filed by Atrium Medical Corporation, Mar. 25, 2013 (70 pages).
Corrected Petition for Inter Partes Review of Claims 24-49 of U.S. Patent No. 7,785,334 under 35 U.S.C. § 312 and 37 C.F.R. § 42.104, filed by Atrium Medical Corporation, Mar. 25, 2013 (70 pages).
Corrected Petition for Inter Partes Review of Claims 50-77 of U.S. Patent No. 7,785,334 under 35 U.S.C. § 312 and 37 C.F.R. § 42.104, filed by Atrium Medical Corporation, Mar. 25, 2013 (70 pages).
Corrected Petition for Inter Partes Review of Claims 99-126 of U.S. Patent No. 7,785,334 under 35 U.S.C. § 312 and 37 C.F.R. § 42.104, filed by Atrium Medical Corporation, Mar. 25, 2013 (69 pages).
Corrected Petition for Inter Partes Review of Claims 1-59 of U.S. Patent No. 7,806,905 under 35 U.S.C. § 312 and 37 C.F.R. § 42.104, filed by Atrium Medical Corporation, Mar. 25, 2013 (69 pages).
Corrected Petition for Inter Partes Review of Claims 60-86 of U.S. Patent No. 7,806,905 under 35 U.S.C. § 312 and 37 C.F.R. § 42.104, filed by Atrium Medical Corporation, Mar. 25, 2013 (69 pages).
Declaration of Adrian Park, M.D., Regarding U.S. Patent No. 7,785,334, Claims 1-23, 78-98, Dated Mar. 13, 2013.
Declaration of Adrian Park, M.D., Regarding U.S. Patent No. 7,785,334, Claims 24-49, Dated Mar. 13, 2013.
Declaration of Adrian Park, M.D., Regarding U.S. Patent No. 7,785,334, Claims 50-77, Dated Mar. 13, 2013.

(56) References Cited

OTHER PUBLICATIONS

Declaration of Adrian Park, M.D., Regarding U.S. Patent No. 7,785,334, Claims 99-126, Dated Mar. 13, 2013.
Declaration of Adrian Park, M.D., Regarding U.S. Patent No. 7,806,905, Claims 1-59, Dated Mar. 13, 2013.
Declaration of Adrian Park, M.D., Regarding U.S. Patent No. 7,806,905, Claims 60-86, Dated Mar. 13, 2013.
File History for U.S. Patent No. 7,785,334, Feb. 17, 2010 Office Action.
File History for U.S. Patent No. 7,785,334, Interview Summary of Apr. 6, 2010 Interview.
File History for U.S. Patent No. 7,785,334, Apr. 12, 2010 Supplemental Amendment.
File History for U.S. Patent No. 7,785,334, Jun. 25, 2010 Notice of Allowance.
File History for U.S. Patent No. 7,806,905, Supplemental Response Filed Apr. 12, 2010.
Fitzgibbons Jr., Robert J. et al., "Laparoscopic Inguinal Herniorrhaphy: Results of a Multicenter Trial," Annals of Surgery 221:3-13 (1995).
Knight, Irving a. et al., "The Repair of Large Incisional Hernias," 108 Calif. Med. 96 (1968).
Park, A. et al., "Laparoscopic Repair of Large Incisional Hernias," Surgical Laparoscopy & Endoscopy 6:123-128 (1996).
510(K) Premarket Notification for the Bard Ventralex Patch, submitted to the FDA on May 23, 2002, and 510(K) Summary and Correspondence, Davol, Inc., K021736 (201 pages).
Petition for Inter Partes Review of Claims 1-59 of U.S. Patent No. 7,806,905 under 35 U.S.C. § 312 and 37 C.F.R. § 42.104, filed by Atrium Medical Corporation (70 pages), Mar. 13, 2013.
Petition for Inter Partes Review of Claims 60-86 of U.S. Patent No. 7,806,905 under 35 U.S.C. § 312 and 37 C.F.R. § 42.104, filed by Atrium Medical Corporation (70 pages), Mar. 13, 2013.
Petition for Inter Partes Review of Claims 1-23 and 78-98 of U.S. Patent No. 7,785,334 under 35 U.S.C. § 312 and 37 C.F.R. § 42.104, filed by Atrium Medical Corporation (70 pages), Mar. 14, 2013
Petition for Inter Partes Review of Claims 24-49 of U.S. Patent No. 7,785,334 under 35 U.S.C. § 312 and 37 C.F.R. § 42.104, filed by Atrium Medical Corporation (70 pages) Mar. 14, 2013.
Petition for Inter Partes Review of Claims 50-77 of U.S. Patent No. 7,785,334 under 35 U.S.C. § 312 and 37 C.F.R. § 42.104, filed by Atrium Medical Corporation (69 pages), Mar. 14, 2013.
Petition for Inter Partes Review of Claims 99-126 of U.S. Patent No. 7,785,334 under 35 U.S.C. § 312 and 37 C.F.R. § 42.104, filed by Atrium Medical Corporation (69 pages), Mar. 14, 2013.
Piskun, G. et al., "Brief Clinical Report: Simplified Technique of Mesh Fixation during Laparoscopic Repair of Abdominal Ventral Hernia," Journal of Laparoendoscopic & Advanced Surgical Techniques 9:193-196 (1999).
Roth, J. Scott et al., "Laparoscopic incisional/ventral herniorrhaphy: a five year experience," Hernia 4:209-214 (1999).
Roth, J. Scott et al., "General Surgery Board Review Manual: Minimally Invasive Abdominal Surgery: An Update," General Surgery, vol. 5, Part 4, 2-11 (1999).
Toy, F. K. et al., "Prospective, multicenter study of laparoscopic ventral hernioplasty: Preliminary results," Surgical Endoscopy 12:955-959 (1998).
Communication, dated Feb. 6, 2013, for European Application No. 10 181 775.7 (6 pages).
Communication, dated Feb. 8, 2013, for European Application No. 10 181 840.9 (5 pages).
Communication, dated Aug. 14, 2013, for European Application No. 10 181 809.4 (6 pages).
Decision, Institution of *Inter Partes* Review, 37 C.F.R. § 42.108, *Atrium Medical Corporation* (Petitioner) v. *Davol Inc.* (Patent Owner), Case IPR2013-00184, Patent 7,806,905, entered Sep. 2, 2013 (24 pages).
Decision, Institution of *Inter Partes* Review, 37 C.F.R. § 42.108, *Atrium Medical Corporation* (Petitioner) v. *Davol Inc.* (Patent Owner), Case IPR2013-00185, Patent 7,806,905, entered Sep. 3, 2013 (22 pages).
Decision, Institution of *Inter Partes* Review, 37 C.F.R. § 42.108, *Atrium Medical Corporation* (Petitioner) v. *Davol Inc.* (Patent Owner), Case IPR2013-00186, Patent 7,785,334 B1, entered Aug. 31, 2013 (39 pages).
Decision, Institution of *Inter Partes* Review, 37 C.F.R. § 42.108, *Atrium Medical Corporation* (Petitioner) v. *Davol Inc.* (Patent Owner), Case IPR2013-00187, Patent 7,785,334 B1, entered Aug. 31, 2013 (36 pages).
Decision, Institution of *Inter Partes* Review, 37 C.F.R. § 42.108, *Atrium Medical Corporation* (Petitioner) v. *Davol Inc.* (Patent Owner), Case IPR2013-00188, Patent 7,785,334 B1, entered Aug. 31, 2013 (35 pages).
Decision, Institution of *Inter Partes* Review, 37 C.F.R. § 42.108, *Atrium Medical Corporation* (Petitioner) v. *Davol Inc.* (Patent Owner), Case IPR2013-00189, Patent 7,785,334 B1, entered Aug. 31, 2013 (37 pages).
Communication, dated Dec. 11, 2013, for European Application No. 10 181 840.9 (4 pages).
Patent Owner's Preliminary Response, *Atrium Medical Corporation* (Petitioner) v. *Davol Inc.* (Patent Owner), Case IPR2013-00184, Patent 7,806,905, entered Jun. 17, 2013, 59 pages.
Patent Owner's Response (Redacted), *Atrium Medical Corporation* (Petitioner) v. *Davol Inc.*(Patent Owner), Case IPR2013-00184, Patent 7,806,905, entered Dec. 4, 2013, 52 pages.
Petitioner's Reply (Redacted), *Atrium Medical Corporation* (Petitioner) v. *Davol Inc.* (Patent Owner), Case IPR2013-00184, Patent 7,806,905, entered Feb. 5, 2014, 17 pages.
Patent Owner's Motion to Exclude Evidence, *Atrium Medical Corporation* (Petitioner) v. *Davol Inc.* (Patent Owner), Case IPR2013-00184, Patent 7,806,905, entered Feb. 27, 2014, 18 pages.
Patent Owner's Motion for Observations on the Cross Examination of Mr. Theodore Karwoski (Redacted), *Atrium Medical Corporation* (Petitioner) v. *Davol Inc.* (Patent Owner), Case IPR2013- 00184, Patent 7,806,905, entered Mar. 7, 2014, 12 pages.
Petitioner's Opposition to Patent Owner's Motion to Exclude Evidence, *Atrium Medical Corporation* (Petitioner) v. *Davol Inc.* (Patent Owner), Case IPR2013-00184, Patent 7,806,905, entered Mar. 13, 2014, 20 pages.
Petitioner's Response to Patent Owner's Motion for Observations on Cross-Examination of Mr. Theodore Karwoski (Redacted), *Atrium Medical Corporation* (Petitioner) v. *Davol Inc.* (Patent Owner), Case IPR2013-00184, Patent 7,806,905, entered Mar. 14, 2014, 12 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00184, Patent 7,806,905, entered Mar. 20, 2014, 9 pages.
Judgment, Termination of the Proceeding, *Atrium Medical Corporation* (Petitioner) v. *Davol Inc.* (Patent Owner), Case IPR2013-00184, Patent 7,806,905, entered Apr. 15, 2014, 6 pages.
Patent Owner's Objections to Evidence Pursuant to 37 C.F.R. § 42.64, *Atrium Medical Corporation* (Petitioner) v. *Davol Inc.* (Patent Owner), Case IPR2013-00184, Patent 7,806,905, entered Feb. 27, 2014, 5 pages.
Second Declaration of Adrian Park M.D., *Atrium Medical Corporation* (Petitioner) v. *Davol Inc.* (Patent Owner), Case IPR2013-00184, Patent 7,806,905, entered Feb. 5, 2014, 4 pages.
Declaration of Theodore Karwoski, *Atrium Medical Corporation* (Petitioner) v. *Davol Inc.* (Patent Owner), Case IPR2013-00184, Patent 7,806,905, entered Feb. 5, 2014, 6 pages.
Declaration of Michael Lee (Redacted), *Atrium Medical Corporation* (Petitioner) v. *Davol Inc.* (Patent Owner), Case IPR2013-00184, Patent 7,806,905, entered Apr. 16, 2014, 8 pages.
Declaration of Guy R. Voeller, M.D., *Atrium Medical Corporation* (Petitioner) v. *Davol Inc.* (Patent Owner), Case IPR2013-00184, Patent 7,806,905, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00184, Patent 7,806,905, entered Dec. 4, 2013, 116 pages.

(56) References Cited

OTHER PUBLICATIONS

Declaration of Rao S. Bezwada, Ph.D., *Atrium Medical Corporation* (Petitioner) v. *Davol Inc.* (Patent Owner), Case IPR2013-00184, Patent 7,806,905, entered Dec. 4, 2013, 12 pages.
Transcript of the Deposition of Guy R. Voeller, M.D., *Atrium Medical Corporation* (Petitioner) v. *Davol Inc.* (Patent Owner), Cases IPR2013-00184-IPR2013-00189, Patents 7,806,905 and 7,785,334, entered Feb. 5, 2014, 134 pages.
Transcript of the Deposition of Karl A. LeBlanc, M.D., *Atrium Medical Corporation* (Petitioner) v. *Davol Inc.* (Patent Owner), Cases IPR2013-00184-IPR2013-00189, Patents 7,806,905 and 7,785,334, entered Feb. 5, 2014, 110 pages.
Transcript of the Deposition of Rao Bezwada, Ph.D., *Atrium Medical Corporation* (Petitioner) v. *Davol Inc.* (Patent Owner), Cases IPR2013-00184-IPR2013-00189, Patents 7,806,905 and 7,785,334, entered Feb. 5, 2014, 115 pages.
Transcript of the Deposition of Michael Lee (Redacted), *Atrium Medical Corporation* (Petitioner) v. *Davol Inc.* (Patent Owner), Cases IPR2013-00184-IPR2013-00189, Patents 7,806,905 and 7,785,334, entered Feb. 5, 2014, 81 pages.
Transcript of the Deposition of Adrian Park, M.D., *Atrium Medical Corporation* (Petitioner) v. *Davol Inc.* (Patent Owner), Cases IPR2013-00184-IPR2013-00189, Patents 7,806,905 and 7,785,334, entered Dec. 4, 2013, 171 pages.
Transcript of the Deposition of Theodore Karwoski (Redacted), vol. 1, *Atrium Medical Corporation* (Petitioner) v. *Davol Inc.* (Patent Owner), Cases IPR2013-00184-IPR2013-00189, Patents 7,806,905 and 7,785,334, entered Apr. 14, 2014, 190 pages.
Patent Owner's Preliminary Response, *Atrium Medical Corporation* (Petitioner) v. *Davol Inc.* (Patent Owner), Case IPR2013-00185, Patent 7,806,905, entered Jun. 17, 2013, 62 pages.
Patent Owner's Response (Redacted), *Atrium Medical Corporation* (Petitioner) v. *Davol Inc.* (Patent Owner), Case IPR2013-00185, Patent 7,806,905, entered Dec. 4, 2013, 59 pages.
Petitioner's Reply (Redacted), *Atrium Medical Corporation* (Petitioner) v. *Davol Inc.* (Patent Owner), Case IPR2013-00185 Patent 7,806,905, entered Feb. 5, 2014, 17 pages.
Patent Owner's Motion for Observations on the Cross-Examination of Mr. Theodore Karwoski (Redacted), *Atrium Medical Corporation* (Petitioner) v. *Davol Inc.* (Patent Owner), Case IPR2013- 00185, Patent 7,806,905, entered Mar. 7, 2014, 12 pages.
Petitioner's Opposition to Patent Owner's Motion to Exclude Evidence, *Atrium Medical Corporation* (Petitioner) v. *Davol Inc.* (Patent Owner), Case IPR2013-00185, Patent 7,806,905, entered Mar. 13, 2014, 20 pages.
Petitioner's Response to Patent Owner's Motion for Observations on Cross-Examination of Mr. Theodore Karwoski (Redacted), *Atrium Medical Corporation* (Petitioner) v. *Davol Inc.* (Patent Owner), Case IPR2013-00185, Patent 7,806,905, entered Mar. 14, 2014, 12 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00185, Patent 7,806,905, entered Mar. 20, 2014, 9 pages.
Judgment, Termination of the Proceeding, *Atrium Medical Corporation* (Petitioner) v. *Davol Inc.* (Patent Owner), Case IPR2013-00185, Patent 7,806,905, entered Apr. 15, 2014, 5 pages.
Patent Owner's Objections to Evidence Pursuant to 37 C.F.R. § 42.64, *Atrium Medical Corporation* (Petitioner) v. *Davol Inc.* (Patent Owner), Case IPR2013-00185, Patent 7,806,905, entered Feb. 27, 2014, 5 pages.
Second Declaration of Adrian Park M.D., *Atrium Medical Corporation* (Petitioner) v. *Davol Inc.* (Patent Owner), Case IPR2013-00185, Patent 7,806,905, entered Feb. 5, 2014, 4 pages.
Declaration of Theodore Karwoski, *Atrium Medical Corporation* (Petitioner) v. *Davol Inc.* (Patent Owner), Case IPR2013-00185, Patent 7,806,905, entered Feb. 5, 2014, 6 pages.
Declaration of Michael Lee (Redacted), *Atrium Medical Corporation* (Petitioner) v. *Davol Inc.* (Patent Owner), Case IPR2013-00185, Patent 7,806,905, entered Dec. 4, 2013, 8 pages.
Declaration of Guy R. Voeller, M.D., *Atrium Medical Corporation* (Petitioner) v. *Davol Inc.* (Patent Owner), Case IPR2013-00185, Patent 7,806,905, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00185, Patent 7,806,905, entered Dec. 4, 2013, 116 pages.
Declaration of Rao S. Bezwada, Ph.D., *Atrium Medical Corporation* (Petitioner) v. *Davol Inc.* (Patent Owner), Case IPR2013-00185, Patent 7,806,905, entered Dec. 4, 2013, 12 pages.
Patent Owner's Preliminary Response, *Atrium Medical Corporation* (Petitioner) v. *Davol Inc.* (Patent Owner), Case IPR2013-00186, Patent 7,785,334, entered Jun. 17, 2013, 66 pages.
Patent Owner's Response (Redacted), *Atrium Medical Corporation* (Petitioner) v. *Davol Inc.* (Patent Owner), Case IPR2013-00186, Patent 7,785,334, entered Dec. 4, 2013, 67 pages.
Petitioner's Reply (Redacted), *Atrium Medical Corporation* (Petitioner) v. *Davol Inc.* (Patent Owner), Case IPR2013-00186 Patent 7,785,334, entered Feb. 5, 2014, 21 pages.
Patent Owner's Motion for Observations on the Cross-Examination of Mr. Theodore Karwoski (Redacted), *Atrium Medical Corporation* (Petitioner) v. *Davol Inc.* (Patent Owner), Case IPR2013- 00186, Patent 7,785,334, entered Mar. 7, 2014, 12 pages.
Petitioner's Opposition to Patent Owner's Motion to Exclude Evidence, *Atrium Medical Corporation* (Petitioner) v. *Davol Inc.* (Patent Owner), Case IPR2013-00186, Patent 7,785,334, entered Mar. 13, 2014, 20 pages.
Petitioner's Response to Patent Owner's Motion for Observations on Cross-Examination of Mr. Theodore Karwoski (Redacted), *Atrium Medical Corporation (Petitioner)* v. *Devol Inc.* (Patent Owner), Case IPR2013-00186, Patent 7,785,334, entered Mar. 14, 2014, 12 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00186, Patent 7,785,334, entered Mar. 20, 2014, 9 pages.
Judgment, Termination of the Proceeding, *Atrium Medical Corporation* (Petitioner) v. *Davol Inc.* (Patent Owner), Case IPR2013-00186, Patent 7,785,334, entered Apr. 15, 2014, 6 pages.
Patent Owner's Objections to Evidence Pursuant to 37 C.F.R. § 42.64, *Atrium Medical Corporation* (Petitioner) v. *Davol Inc.* (Patent Owner), Case IPR2013-00186, Patent 7,785,334, entered Feb. 27, 2014, 5 pages.
Second Declaration of Adrian Park M.D., *Atrium Medical Corporation* (Petitioner) v. *Davol Inc.* (Patent Owner), Case IPR2013-00186, Patent 7,785,334, entered Feb. 5, 2014, 4 pages.
Declaration of Theodore Karwoski, *Atrium Medical Corporation* (Petitioner) v. *Davol Inc.* (Patent.Owner), Case IPR2013-00186, Patent 7,785,334, entered Feb. 5, 2014, 6 pages.
Declaration of Donna Torres (Redacted), *Atrium Medical Corporation* (Petitioner) v. *Davol Inc.* (Patent Owner), Case IPR2013-00186, Patent 7,785,334, entered Dec. 4, 2013, 5 pages.
Declaration of Valerie Grahn, née Vadurro (Redacted), *Atrium Medical Corporation* (Petitioner) v. *Davol Inc.* (Patent Owner), Case IPR2013-00186, Patent 7,785,334, entered Dec. 4, 2013, 2 pages.
Declaration of James Mello (Redacted), *Atrium Medical Corporation* (Petitioner) v. *Davol Inc.* (Patent Owner), Case IPR2013-00186, Patent 7,785,334, entered Dec. 4, 2013, 2 pages.
Declaration of Michael Lee (Redacted), *Atrium Medical Corporation* (Petitioner) v. *Davol Inc.* (Patent Owner), Case IPR2013-00186, Patent 7,785,334, entered Dec. 4, 2013, 8 pages.
Declaration of Guy R. Voeller, M.D., *Atrium Medical Corporation* (Petitioner) v. *Davol Inc.* (Patent Owner), Case IPR2013-00186, Patent 7,785,334, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00186, Patent 7,785,334, entered Dec. 4, 2013, 116 pages.
Declaration of Rao S. Bezwada, Ph.D., *Atrium Medical Corporation* (Petitioner) v. *Davol Inc.* (Patent Owner), Case IPR2013-00186, Patent 7,785,334, entered Dec. 4, 2013, 12 pages.
Declaration of Adrian Park, M.D., *Atrium Medical Corporation* (Petitioner) v. *Davol Inc.* (Patent.Owner), Case IPR2013-00186, Patent 7,785,334, entered Dec. 4, 2013, 58 pages.

(56) References Cited

OTHER PUBLICATIONS

Transcript of the Deposition of Donna Tones (Redacted), *Atrium Medical Corporation* (Petitioner) v. *Davol Inc.* (Patent Owner), Cases IPR2013-00186 and IPR2013-00187, Patent 7,785,334, entered Feb. 5, 2014, 189 pages.
Transcript of the Deposition of Valerie Grahn, née Vadurro (Redacted), *Atrium Medical Corporation* (Petitioner) v. *Davol Inc.* (Patent Owner), Cases IPR2013-00186 and IPR2013-00187, Patent 7,785,334, entered Feb. 5, 2014, 29 pages.
Transcript of the Deposition of James Mello (Redacted), *Atrium Medical Corporation* (Petitioner) v. *Davol Inc.* (Patent Owner), Cases IPR2013-00186-00187, Patent 7,785,334, entered Feb. 5, 2014, 29 pages.
Patent Owner's Preliminary Response, *Atrium Medical Corporation* (Petitioner) v. *Davol Inc.* (Patent Owner), Case IPR2013-00187, Patent 7,785,334, entered Jun. 17, 2013, 63 pages.
Patent Owner's Response (Redacted), *Atrium Medical Corporation* (Petitioner) v. *Davol Inc.* (Patent Owner), Case IPR2013-00187, Patent 7,785,334, entered Dec. 4, 2013, 67 pages.
Petitioner's Reply (Redacted), *Atrium Medical Corporation* (Petitioner) v. *Davol Inc.* (Patent Owner), Case IPR2013-00187, Patent 7,785,334, entered Feb. 6, 2014, 20 pages.
Patent Owner's Motion for Observations on the Cross-Examination of Mr. Theodore Karwoski (Redacted), *Atrium Medical Corporation* (Petitioner) v. *Davol Inc.* (Patent Owner), Case IPR2013- 00187, Patent 7,785,334, entered Mar. 7, 2014, 12 pages.
Petitioner's Opposition to Patent Owner's Motion to Exclude Evidence, *Atrium Medical Corporation* (Petitioner) v. *Davol Inc.* (Patent Owner), Case IPR2013-00187, Patent 7,785,334, entered Mar. 13, 2014, 20 pages.
Petitioner's Response to Patent Owner's Motion for Observations on Cross-Examination of Mr. Theodore Karwoski (Redacted), *Atrium Medical Corporation* (Petitioner) v. *Davol Inc.* (Patent Owner), Case IPR2013-00187, Patent 7,785,334, entered Mar. 14, 2014, 12 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00187, Patent 7,785,334, entered Mar. 20, 2014, 9 pages.
Judgment, Termination of Proceeding, *Atrium Medical Corporation* (Petitioner) v. *Davol Inc.* (Patent Owner), Case IPR2013-00187, Patent 7,785,334, entered Apr. 15, 2014, 6 pages.
Patent Owner's Objections to Evidence, *Atrium Medical Corporation* (Petitioner) v. *Davol Inc.* (Patent Owner), Case IPR2013-00187, Patent 7,806,905, entered Feb. 27, 2014, 5 pp.
Second Declaration of Adrian Park M.D., *Atrium Medical Corporation* (Petitioner) v. *Davol Inc.* (Patent Owner), Case IPR2013-00187, Patent 7,785,334, entered Feb. 6, 2014, 4 pages.
Declaration of Theodore Karwoski, *Atrium Medical Corporation* (Petitioner) v. *Davol Inc.* (Patent Owner), Case IPR2013-00187, Patent 7,785,334, entered Feb. 6, 2014, 6 pages.
Declaration of Guy R. Voeller, M.D., *Atrium Medical Corporation* (Petitioner) v. *Davol Inc.* (Patent Owner), Case IPR2013-00187, Patent 7,785,334, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00187, Patent 7,785,334, entered Dec. 4, 2013, 116 pages.
Declaration of Rao S. Bezwada, Ph.D., *Atrium Medical Corporation* (Petitioner) v. *Davol Inc.* (Patent Owner), Case IPR2013-00187, Patent 7,785,334, entered Dec. 4, 2013, 12 pages.
Declaration of Adrian Park, M.D., *Atrium Medical Corporation* (Petitioner) v. *Davol Inc.* (Patent Owner), Case IPR2013-00187, Patent 7,785,334, entered Dec. 4, 2013, 58 pages.
Declaration of Donna Torres (Redacted), *Atrium Medical Corporation* (Petitioner) v. *Davol Inc.* (Patent Owner), Case IPR2013-00187, Patent 7,785,334, entered Dec. 4, 2013, 5 pages.
Declaration of Valerie Grahn, nee Vadurro (Redacted), *Atrium Medical Corporation* (Petitioner) v. *Davol Inc.* (Patent Owner), Case IPR2013-00187, Patent 7,785,334, entered Dec. 4, 2013, 2 pages.
Declaration of James Mello (Redacted), *Atrium Medical Corporation* (Petitioner) v. *Davol Inc.* (Patent Owner), Case IPR2013-00187, Patent 7,785,334, entered Dec. 4, 2013, 2 pages.
Declaration of Michael Lee (Redacted), *Atrium Medical Corporation* (Petitioner) v. *Davol Inc.* (Patent Owner), Case IPR2013-00187, Patent 7,785,334, entered Dec. 4, 2013, 8 pages.
Patent Owner's Preliminary Response, *Atrium Medical Corporation* (Petitioner) v. *Davol Inc.* (Patent Owner), Case IPR2013-00188, Patent 7,785,334, entered Jun. 17, 2013, 60 pages.
Patent Owner's Response (Redacted), *Atrium Medical Corporation* (Petitioner) v. *Davol Inc.* (Patent Owner), Case IPR2013-00188, Patent 7,785,334, entered Dec. 4, 2013, 65 pages.
Petitioner's Reply (Redacted), *Atrium Medical Corporation* (Petitioner) v. *Davol Inc.* (Patent Owner), Case IPR2013-00188, Patent 7,785,334, entered Feb. 6, 2014, 16 pages.
Patent Owner's Motion for Observations on the Cross-Examination of Mr. Theodore Karwoski (Redacted), *Atrium Medical Corporation* (Petitioner) v. *Davol Inc.* (Patent Owner), Case IPR2013-00188, Patent 7,785,334, entered Mar. 7, 2014, 12 pages.
Petitioner's Opposition to Patent Owner's Motion to Exclude Evidence, *Atrium Medical Corporation* (Petitioner) v. *Davol Inc.* (Patent Owner), Case IPR2013-00188, Patent 7,785,334, entered Mar. 13, 2014, 20 pages.
Petitioner's Response to Patent Owner's Motion for Observations on Cross-Examination of Mr. Theodore Karwoski (Redacted), *Atrium Medical Corporation* (Petitioner) v. *Davol Inc.* (Patent Owner), Case IPR2013-00188, Patent 7,785,334, entered Mar. 14, 2014, 12 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00188, Patent 7,785,334, entered Mar. 20, 2014, 9 pages.
Judgment, Termination of the Proceeding, *Atrium Medical Corporation* (Petitioner) v. *Davol Inc.* (Patent Owner), Case IPR2013-00188, Patent 7,785,334, entered Apr. 15, 2014, 5 pages.
Patent Owner's Objections to Evidence Pursuant to 37 C.F.R. § 42.64, *Atrium Medical Corporation* (Petitioner) v. *Davol Inc.* (Patent Owner), Case IPR2013-00188, Patent 7,806,905, entered Feb. 27, 2014, 5 pages.
Second Declaration of Adrian Park M.D., *Atrium Medical Corporation* (Petitioner) v. *Davol Inc.* (Patent Owner), Case IPR2013-00188, Patent 7,785,334, entered Feb. 6, 2014, 4 pages.
Declaration of Theodore Karwoski, *Atrium Medical Corporation* (Petitioner) v. *Davol Inc.* (Patent Owner), Case IPR2013-00188, Patent 7,785,334, entered Feb. 6, 2014, 6 pages.
Declaration of Michael Lee (Redacted), *Atrium Medical Corporation* (Petitioner) v. *Davol Inc.* (Patent Owner), Case IPR2013-00188, Patent 7,785,334, entered Dec. 4, 2013, 8 pages.
Declaration of Guy R. Voeller, M.D., *Atrium Medical Corporation* (Petitioner) v. *Davol Inc.* (Patent Owner), Case IPR2013-00188, Patent 7,785,334, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00188, Patent 7,785,334, entered Dec. 4, 2013, 116 pages.
Declaration of Rao S. Bezwada, Ph.D., *Atrium Medical Corporation* (Petitioner) v. *Davol Inc.* (Patent Owner), Case IPR2013-00188, Patent 7,785,334, entered Dec. 4, 2013, 12 pages.
Declaration of Adrian Park, M.D., *Atrium Medical Corporation* (Petitioner) v. *Davol Inc.* (Patent Owner), Case IPR2013-00188, Patent 7,785,334, entered Dec. 4, 2013, 58 pages.
Patent Owner's Preliminary Response, *Atrium Medical Corporation* (Petitioner) v. *Davol Inc.* (Patent Owner), Case IPR2013-00189, Patent 7,785,334, entered Jun. 17, 2013, 58 pages.
Patent Owner's Response (Redacted), *Atrium Medical Corporation* (Petitioner) v. *Davol Inc.* (Patent Owner), Case IPR2013-00189, Patent 7,785,334, entered Dec. 4, 2013, 66 pages.
Petitioner's Reply (Redacted), *Atrium Medical Corporation* (Petitioner) v. *Davol Inc.* (Patent Owner), Case IPR2013-00189, Patent 7,785,334, entered Feb. 6, 2014, 16 pages.
Patent Owner's Motion for Observations on the Cross-Examination of Mr. Theodore Karwoski (Redacted), *Atrium Medical Corporation* (Petitioner) v. *Davol Inc.* (Patent Owner), Case IPR2013- 00189, Patent 7,785,334, entered Mar. 7, 2014, 12 pages.

(56) References Cited

OTHER PUBLICATIONS

Petitioner's Opposition to Patent Owner's Motion to Exclude Evidence, *Atrium Medical Corporation* (Petitioner) v. *Davol Inc.* (Patent Owner), Case IPR2013-00189, Patent 7,785,334, entered Mar. 13, 2014, 20 pages.
Petitioner's Response to Patent Owner's Motion for Observations on Cross-Examination of Mr. Theodore Karwoski (Redacted), *Atrium Medical Corporation* (Petitioner) v. *Davol Inc.* (Patent Owner), Case IPR2013-00189, Patent 7,785,334, entered Mar. 14, 2014, 20 pages.
Reply in Support of Patent Owner's Motion to Exclude Evidence Under 37 C.F.R. § 42.64, *Atrium Medical Corporation* (Petitioner) v. *Davol Inc.* (Patent Owner), Case IPR2013-00189, Patent 7,785,334, entered Mar. 20, 2014, 9 pages.
Judgment, Termination of the Proceeding, *Atrium Medical Corporation* (Petitioner) v. *Davol Inc.* (Patent Owner), Case IPR2013-00189, Patent 7,785,334, entered Apr. 15, 2014, 5 pages.
Patent Owner's Objections to Evidence Pursuant to 37 C.F.R. § 42.64, *Atrium Medical Corporation* (Petitioner) v. *Davol Inc.* (Patent Owner), Case IPR2013-00189, Patent 7,806,905, entered Feb. 27, 2014, 5 pages.
Second Declaration of Adrian Park M.D., Atrium Medical Corporation (Petitioner) v. Davol Inc. (Patent Owner), Case IPR2013-00189, Patent 7,785,334, entered Feb. 6, 2014, 4 pp.
Declaration of Theodore Karwoski, *Atrium Medical Corporation* (Petitioner) v. *Davol Inc.* (Patent Owner), Case IPR2013-00189, Patent 7,785,334, entered Feb. 6, 2014, 6 pages.
Declaration of Michael Lee (Redacted), *Atrium Medical Corporation* (Petitioner) v. *Davol Inc.* (Patent Owner), Case IPR2013-00189, Patent 7,785,334, entered Dec. 4, 2013, 8 pages.
Declaration of Guy R. Voeller, M.D., *Atrium Medical Corporation* (Petitioner) v. *Davol Inc.* (Patent Owner), Case IPR2013-00189, Patent 7,785,334, entered Dec. 4, 2013, 151 pages.
Declaration of Karl A. LeBlanc, M.D., *Atrium Medical Corporation* (Petitioner) v. *Davol Inc.* (Patent Owner), Case IPR2013-00189, Patent 7,785,334, entered Dec. 4, 2013, 116 pages.
Declaration of Rao S. Bezwada, Ph.D., *Atrium Medical Corporation* (Petitioner) v. *Davol Inc.* (Patent Owner), Case IPR2013-00189, Patent 7,785,334, entered Dec. 4, 2013, 12 pages.
Bittner et al., Chapter 8: Transabdominal pre-peritoneal approach. Laporoscopic Hernia Surgery: An Operative Guide. 2003:53-64.
Collaborative Faculty—Davol, available at http://www.davol.com/surgical-education/collaborative-faculty/. 2 pages. Accessed Jan. 15, 2014.
ConMed 510(K) Summary for Y-KNOT Flex All-Suture Anchor, dated Jul. 2, 2013, 5 pages.
Curcillo, Laparoscopic ventral hernia repair with self-expanding mesh—a "one stitch, two port" technique. Hernia Repair Presentation. American Hernia Society. May 8-12, 2002. Abstract #19, 22 pages.
Definition of "Element," Webster's Third New International Dictionary. Philip Babcock Gove, ed.-in-chief, 1993: p. 734.
Definition of "Strap," Merriam-Webster's Collegiate Dictionary. $10^{th}$ ed. 1999:1162.
Definition of "Usual," The American Heritage Dictionary. $4^{th}$ ed., Houghton Mifflin Company. 2000. 3 pages. www.thefreedictionary.com/usual.
Definition of "Usually," Random House Dictionary, 2013, and Collins English Dictionary, $10^{th}$ ed., 2009. dictionary.reference.com/browse/usually.
Ethicon Patch Instructions, Nov. 23, 2013, 7 pages.
Hawes, The repair of hernias with ribbon-gut: summary of twenty-six cases. Am J Surg. 1938;41(3):509-511.'.
Kingsnorth et al., Ch 6: Principles in Hernia Surgery and Ch 25: Complications of Hernia Repair. In Management of Abdominal Hernias, $3^{rd}$ ed. 2003: 69-77 and 307-326.
Provisional Application Filed by John Allen Pacey on Jan. 30, 2001. Percutaneous catheter delivery system for inguinal hernia patch.
Ribbon Gut: Its Description and Uses. Brooklyn, New York: Davis & Geck, Inc. 1940:1-2; 18-21 ("Ribbon Gut Book"). 9 pages.
Selected Pages from the United States Pharmacopeia, The National Formulary. Official from Jan. 1, 2002. 6 pages.
Ventralex Hernia Patch, Umbilical Hernia Repair Marketing Brochure, 2009, 4 pages.
Ventralex Hernia Patch, Umbilical Hernia Repair Marketing Brochure, 2009, 10 pages.
Ventralex Hernia Patch, Umbilical Hernia Repair Technique Guide, 2009, 16 pages.
Ventralex Patch Instructions, Jul. 16, 2002, 201 pages.
Ventralex Sales Revenue Chart (Redacted), 2002-YTD 2013, 1 page.
Xiros 510(K) Summary for Poly-Tapes. Aug. 28, 2001. (Revised Aug. 16, 2001). 7 pages.

\* cited by examiner

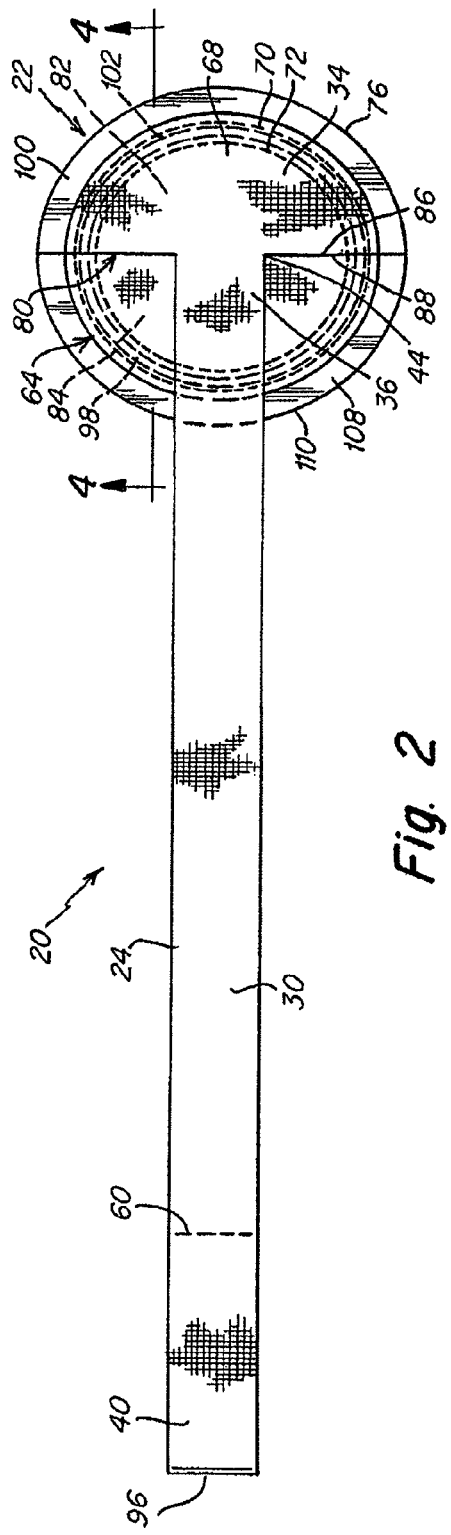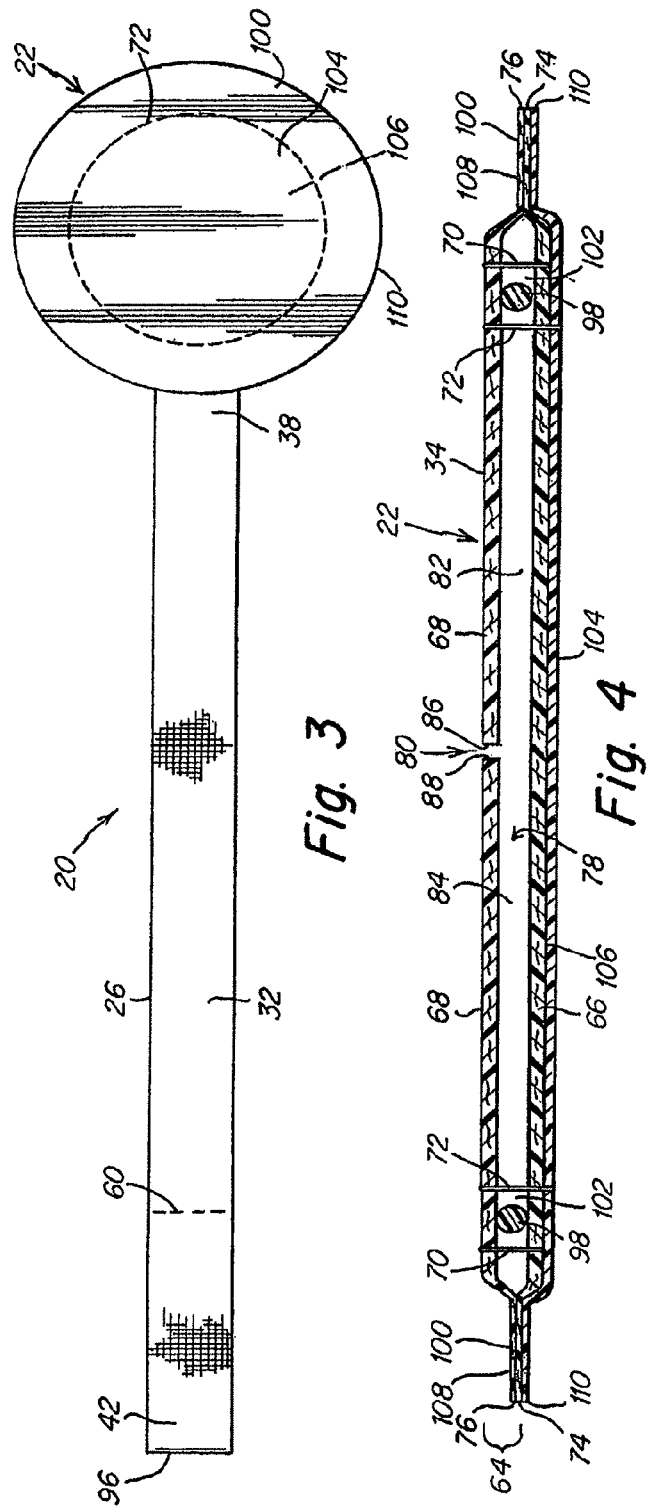

IMPLANTABLE PROSTHESIS

This application is a continuation of U.S. application Ser. No. 11/508,447, filed Aug. 23, 2006, which is a continuation of U.S. application Ser. No. 10/212,006, filed Aug. 2, 2002.

FIELD OF THE INVENTION

The present invention relates to an implantable prosthesis and, more particularly, to a prosthesis for repairing or augmenting openings and/or weaknesses in a soft tissue or muscle wall.

DISCUSSION OF RELATED ART

Various prosthetic repair materials are known for repairing and reinforcing anatomical defects, such as soft tissue and muscle wall hernias. For example, in connection with a repair of an umbilical hernia, it is common for a surgeon to place a sheet of prosthetic repair fabric beneath the opening to the defect ("underlay"), above the opening to the defect ("overlay"), or to form the fabric into a three-dimensional shape, such as in the form of a cone or cylinder to "plug" the rupture. It has been recognized that puncture tracts created in laparoscopic surgery as a passageway for delivering instruments and prostheses to a surgical site may be susceptible to later herniation. Closure of the laparoscopic puncture is typically done with a series of sutures through the skin and/or underlying tissue and muscle, with or without the aid of a fabric-type or other type of prosthesis. Use of repair sutures at the puncture wound opening may potentially lead to complications of nerve entrapment, vessel injury, or subsequent hernia at the defect site.

It has been suggested for certain procedures to repair an anatomical defect using a prosthetic fabric without reapproximating the edges of the anatomical defect. For example, U.S. Pat. No. 5,397,331 to Himpens et al. proposes to repair a weakness of the abdominal wall produced by a trocar sheath using a prosthesis that includes a layer of prosthetic material for covering the weakness and a resilient stiffener for spreading the layer of material into a planar configuration. A thread extends from the repair device for routing through the trocar sheath so that a slight pull of the thread draws the repair device against the peritoneum. Upon removal of the trocar sheath, the thread may subsequently be fastened on the skin surface to hold the prosthesis in position.

U.S. Pat. No. 5,836,961 to Kieturakis et al. proposes to repair a hernia defect with a patch that includes a disk and a tail that is secured to and extends from the disk. The patch is inserted into a patient using conventional laparoscopic instruments, and the tail is attached to a distal portion of an inguinal hernia sac. The hernia sac is then separated and the pressure of the insufflation gas causes the tail of the patch to be pulled upwardly into the inguinal ring to draw the disk against the inguinal ring.

It is an object of the present invention to provide an improved method and prosthesis for repairing and reinforcing soft tissue or muscle walls.

SUMMARY OF THE INVENTION

The present invention relates to an implantable prosthesis for repairing an anatomical defect, such as a tissue or muscle wall hernia, including an umbilical hernia, and for preventing the occurrence of a hernia at a small opening or weakness in a tissue or muscle wall, such as at a puncture tract opening remaining after completion of a laparoscopic procedure.

In one embodiment, an implantable prosthesis includes a body portion of implantable, biologically compatible material that is constructed and arranged to cover at least a portion of the tissue or muscle wall defect, and at least one tether extending from the body portion and having a cross-section with a width and thickness, the width being greater than the thickness. The at least one tether has a length that is sufficient to extend through the tissue or muscle wall defect and to be accessible from outside the patient when the body portion is positioned over the defect. The length of the at least one tether is at least 2.5 inches.

In another embodiment, an implantable prosthesis is provided for repairing an existing or potential tissue or muscle wall defect. The implantable prosthesis comprises a body portion of an implantable, biologically compatible material that is constructed and arranged to cover at least a portion of the tissue or muscle wall defect, and first and second straps extending from the body portion. The first and second straps are constructed and arranged to extend through the tissue or muscle wall defect when the body portion is positioned over the defect. Each of the first and second straps has a cross-section with a width and thickness, the width being greater than the thickness.

In yet another embodiment, an implantable prosthesis is provided for repairing an existing or potential tissue or muscle wall defect. The implantable prosthesis includes a patch of repair fabric that is constructed and arranged to cover at least a portion of the tissue or muscle wall defect, a resilient support member disposed on the patch to urge the patch to a planar configuration, and at least one tether of repair fabric that is susceptible to tissue and muscle integration. The at least one tether extends from the patch and is constructed and arranged to extend through the tissue or muscle wall defect when the patch is positioned over the defect.

In a further embodiment, an implantable prosthesis is provided for repairing an existing or potential tissue or muscle wall defect. The implantable prosthesis comprises a patch of repair fabric that is constructed and arranged to cover at least a portion of the tissue or muscle wall defect, a resilient support member disposed on the patch, and at least one strap extending from the patch. The resilient support member is constructed and arranged to urge the patch into a planar configuration. The at least one strap is constructed and arranged to extend through the tissue or muscle wall defect when the patch is positioned over the defect. The at least one strap has a cross-section with a width and thickness, the width being greater than the thickness.

In another embodiment, an implantable prosthesis is provided for repairing an existing or potential tissue or muscle wall defect. The implantable prosthesis comprises a body portion of implantable, biologically compatible material that is constructed and arranged to cover at least a portion of the tissue or muscle wall defect, and at least one tether extending from the body portion and being constructed and arranged to extend through the tissue or muscle wall defect when the body portion is positioned over the defect. The prosthesis also comprises an indicator disposed on the at least one tether at a predetermined location to indicate a position of the body portion relative to a reference location.

In yet another embodiment, an implantable prosthesis is provided for repairing an existing or potential tissue or muscle wall defect. The implantable prosthesis comprises a patch of repair fabric that is constructed and arranged to cover at least a portion of the tissue or muscle wall defect, and at least one tether extending from the patch and being constructed and arranged to extend through the tissue or muscle wall defect when the patch is positioned over the defect. The patch includes first and second layers of repair fabric that are joined to each other to create a pocket therebetween. The patch has an access opening that is adapted to provide entry into an interior of the pocket to facilitate positioning of the patch over the tissue or muscle wall defect.

In a further embodiment, an implantable prosthesis is provided for repairing an existing or potential tissue or muscle wall defect. The implantable prosthesis comprises at least one layer of repair fabric that is susceptible to the formation of adhesions with tissue and organs, and a resilient support member disposed on the at least one layer of repair fabric. The at least one layer of repair fabric is constructed and arranged to cover at least a portion of the tissue or muscle wall defect. The at least one layer of repair fabric has a first surface for facing the tissue or muscle wall defect and a second surface for facing away from the tissue or muscle wall defect. The resilient support member is constructed and arranged to urge the at least one layer of repair fabric into a planar configuration. The prosthesis also comprises first and second straps extending from the first surface of the at least one layer of repair fabric. The first and second straps have a length that is sufficient to extend through the tissue or muscle wall defect and outside the patient when the at least one layer of repair fabric is positioned over the defect. Each of the first and second straps has a cross-section with a width and thickness, the width being greater than the thickness.

In still another embodiment, a method is provided to repair an existing or potential tissue or muscle wall defect in a patient. The method comprises providing an implantable prosthesis that includes a patch of repair fabric that is constructed and arranged to cover at least a portion of the tissue or muscle wall defect, and at least one strap of repair fabric extending from the patch and being constructed and arranged to extend through the tissue or muscle wall defect and protrude outside the patient when the patch is positioned over the defect. The at least one strap has a cross-section with a width and thickness, the width being greater than the thickness. The method also comprises introducing the patch into the patient; routing the at least one strap to extend through the defect and to a region that is accessible from outside the patient; and positioning the patch over the defect.

Various embodiments of the present invention provide certain advantages and overcome certain drawbacks of prior prostheses. Embodiments of the invention may not share the same advantages, and those that do may not share them under all circumstances. This being said, the present invention provides numerous advantages including the added advantages of ease of implantation, promotion of desired tissue or muscle ingrowth without involving surrounding tissue or organs, and reduction of tension at the defect side.

Further features and advantages of the present invention, as well as the structure of various embodiments, are described in detail below with reference to the accompanying drawings.

BRIEF DESCRIPTION OF THE DRAWINGS

Various embodiments of the invention will now be described, by way of example, with reference to the accompanying drawings, in which:

FIG. 2 is a top plan view of an implantable prosthesis in accordance with another illustrative embodiment of the present invention;

FIG. 3 is a bottom plan view of the prosthesis of FIG. 2;

FIG. 4 is a cross-sectional view of a portion of the prosthesis taken along section line 4-4 of FIG. 2;

DESCRIPTION OF ILLUSTRATIVE EMBODIMENTS

Figure 1:
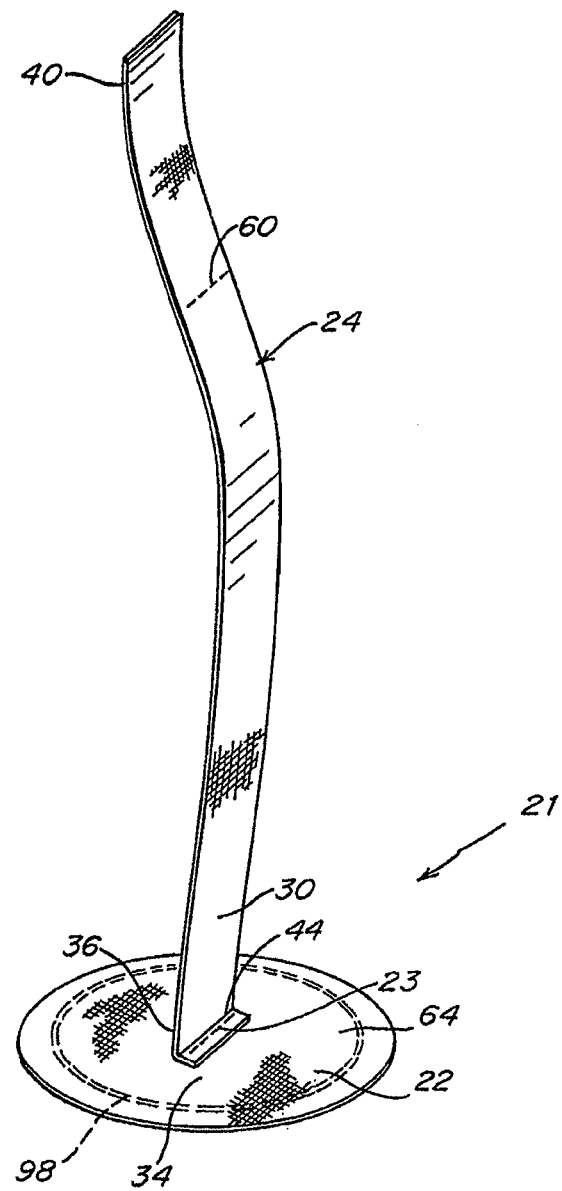
FIG. 1 is a top perspective view of an implantable prosthesis in accordance with one illustrative embodiment of the present invention.
Figure 5:
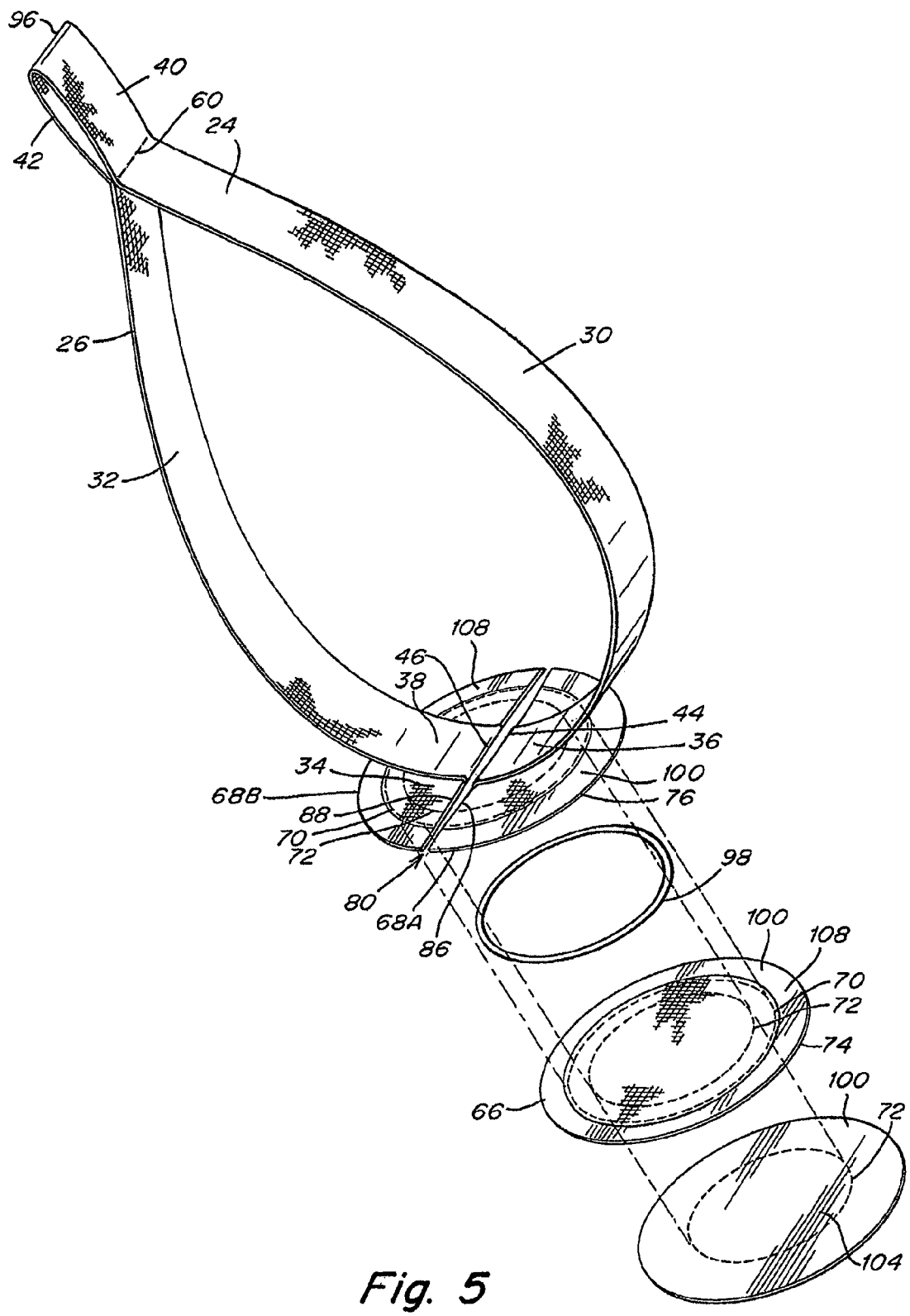
FIG. 5 is an exploded top perspective view of the prosthesis of FIG. 2.
Figure 6:
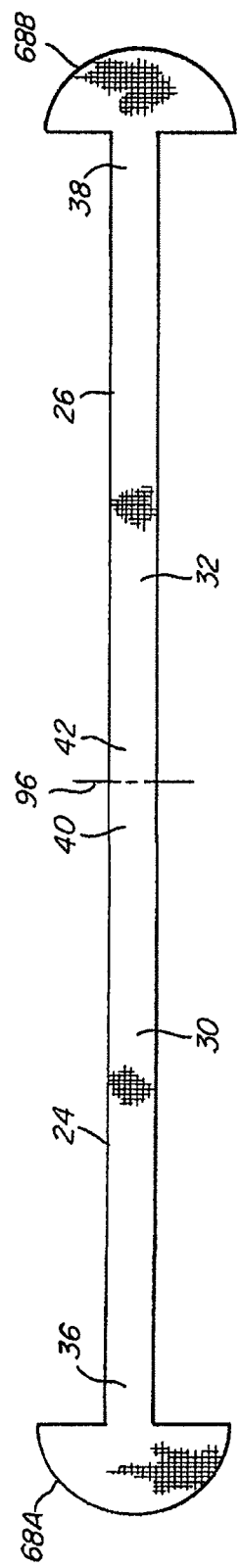
FIG. 6 is a top plan view of a layer of repair fabric for fabricating the tethers of the prosthesis of FIG. 2.

The invention is directed to an implantable prosthesis for repairing or augmenting anatomical defects, and is particularly suitable for the repair of openings in, and weaknesses of soft tissue and muscle walls or other anatomical regions. For ease of understanding, and without limiting the scope of the invention, the prosthesis to which this patent is addressed is described below particularly in connection with the prophylactic repair of a trocar wound created during laparoscopic surgery and with the repair of an umbilical hernia. It should be understood, however, that the prosthesis is not so limited and may be employed in other anatomical procedures, as would be apparent to one of skill in the art. For example, the prosthesis may be used for the repair or augmentation of a tissue or muscle wall hernia, such as an incisional hernia, an inguinal hernia, a ventral hernia, a femoral hernia, and other tissue or muscle wall openings, as well as other puncture wounds or defects in addition to those formed by, and then left on removal of, a trocar and/or cannula.

The invention is more particularly directed to a repair device that includes a patch or plug having a body portion that is larger than at least a portion of the opening or weakness so that placement of the body portion against the defect will cover or extend across that portion of the opening or weakness. The repair device further includes at least one tether that extends from the patch or plug and may be manipulated by a surgeon to position the patch or plug relative to the repair site and/or to secure the patch or plug relative to the opening or weakness in the tissue or muscle wall. The tether may be configured to extend through the defect and outside a patient's body to allow a surgeon to position and/or manipulate the patch from a location outside the body. A portion of the tether may be attached directly to anatomy surrounding the edges of the defect opening or to other neighboring tissue, muscle, skin or other anatomy, using a suture, staple, tack or other attachment device whether separate from or integrally formed with the tether, so as to anchor the patch in place. Any excess tether may then be removed.

An indicator may be arranged on the tether to aid a surgeon in determining when the patch or plug has been inserted a sufficient depth or distance within a patient. The indicator may be located a desired distance from the patch or plug such that its location relative to a reference location provides an indication as to the position of the patch or plug within the patient without direct visualization of the patch or plug.

The tether may be configured as a strap having a cross-section with a width that is greater than its thickness. The strap configuration presents a relatively large surface area for the tether that may enhance the amount of tissue integration to the tether, if desired. The strap configuration may also, or alternatively, act to distribute applied forces acting on the tether across a relatively large area of the patch or plug as compared to a small area of the patch or plug as could occur if the tether was in the form of a length of suture material. The width of the tether may extend across a portion or approximate the width of the body portion of the patch or plug. However, it should be appreciated that the invention is not limited in this respect, and the tether may have any suitable width, and its width may vary along the length of the tether.

The tether may be joined to the patch or plug at one or more junctions so that forces acting through the tether may be applied to the patch or plug at those junctions. Multiple tethers may be joined to the patch or plug to enhance the positioning and anchoring of the patch or plug.

The tether may be configured from an elongated strip of a biologically compatible, implantable material, such as a knit fabric, or may be solid or substantially non-porous. The tether may be formed of a fabric that either enhances tissue integration, inhibits adhesions with tissue, or is a combination of both, as desired. The material of the tether may be permanent or absorbable. The patch or plug, similarly, may be formed of a tissue infiltratable material such as a knit fabric, or may be composed of a solid or substantially non-porous material. The tether and/or the patch or plug may be formed of one or more layers of the same or dissimilar material. The tether and the patch or plug may be formed with portions that are tissue infiltratable and other portions that are non-tissue infiltratable, providing selected areas of the repair device with different tissue ingrowth and adhesion resistant properties.

The repair device may be placed at the defect site using an open surgical procedure, by laparoscopically passing the patch or plug through a cannula that extends along a puncture tract leading to the defect, such as may be formed naturally or by a trocar, or through a hybrid procedure where an incision is formed through the skin and then a tract is created in the underlying tissue and/or muscle leading to the defect site along which the repair device is transported. The patch or plug may be flexible, allowing reduction of the repair device, such as by folding, rolling or otherwise collapsing the patch or plug, into a slender configuration suitable for delivery along the puncture tract, or a cannula extending through the puncture tract, to the defect site. Upon exiting the puncture tract or cannula, the patch or plug may automatically unfurl or may be unfolded, unrolled or otherwise deployed by the surgeon to an unfurled or expanded configuration suitable to repair the weakness or opening.

A support member may be arranged in or on the patch or plug to help deploy the patch or plug at the surgical site and/or help inhibit collapse or buckling of the patch or plug. The support member may be configured as a complete or partial loop or a ring, criss-cross, x-shape, or any other suitable arrangement that helps to maintain a desired shape, and/or position, of the patch or plug despite tension forces that may be applied on the repair device through the tether. The support member may be rollable, foldable or otherwise collapsible, when the patch or plug is reduced in size for puncture tract or cannula delivery, and may spring back, either automatically or upon the influence of a force (e.g., body heat where the support is formed of a shape memory material, such as NITINOL) to its expanded shape on deployment at the repair site, influencing the patch or plug to assume its unfurled or expanded configuration.

The patch or plug may be configured with a pocket or cavity to facilitate the deployment and/or positioning of the patch or plug over the opening or weakness. An access opening may be provided to allow access to the interior of the pocket. In this manner, the surgeon may place one or more fingers or an instrument through the access opening and into the pocket to ensure proper deployment and placement of the patch or plug.

FIG. 1 illustrates one embodiment of a prosthesis 21 for repairing or augmenting soft tissue and muscle wall defects, such as an umbilical hernia or a trocar wound created in the abdominal wall of a patient during a laparoscopic surgery.

The prosthesis 21 includes a body portion 22 of implantable, biologically compatible material that is configured to cover at least a portion of the defect. As shown, the body portion includes a patch that may be used as an underlay or an overlay. The patch may be configured with any desired strength, flexibility, tissue integration, adhesion resistance and/or other characteristics suitable for the repair as would be apparent to one of skill. Although the body portion of the prosthesis is described in connection with a patch-type embodiment, the body portion may include a plug, a combination plug and patch, and other suitable arrangements for mending the defect.

The prosthesis also includes a tether 24 extending from the patch 22 to facilitate positioning and/or anchoring of the patch within a patient's body. As shown, the tether extends from a surface 34 of the patch that is to face the defect 28 when the patch 22 is implanted in the patient's body. In this manner, the tether may be routed through the defect and manipulated to position the patch over the defect. It should be appreciated that the tether may extend from any suitable portion of the patch. Additionally, two or more tethers may be provided on the patch.

Since many tissue and muscle wall defects are relatively small and/or space may be limited at the defect site, access to the patch either directly or using tools may be difficult for manipulating and/or positioning it over the defect. Consequently, the tether 24 may be configured to extend through the anatomical defect to a location that is readily accessible to the surgeon either within or outside the patient's body. In this manner, the surgeon may grasp and manipulate the proximal end 40 of the tether to position the patch within the body and against the defect. For example, after the patch is deployed at the defect site, the surgeon may pull on the tether to draw the patch into position over the defect.

In certain procedures, including laparoscopic and open repair procedures, the surgeon may desire to manipulate the patch 22 from outside the patient's body. In this regard, the elongated tether 22 may be configured with a length that is sufficient to extend from the implanted patch, through the defect and to a region that is accessible from outside of the body of the patient. Preferably, the tether is sized so that it protrudes outside the patient's body when the prosthesis is implanted at the defect site to provide ready access to the tether by the surgeon.

The length of the tether may be dictated by the location of the defect and/or the repair procedure. For example, a short tether may be sufficient for repairing an umbilical hernia using open surgery, while a longer tether may be desired for a laparoscopic procedure in which the tether extends through a cannula. In one illustrative embodiment, the tether 24 may be configured with a length that ranges from approximately 2.5 inches to approximately 20 inches. In one embodiment for repairing an umbilical hernia, the length of the tether is at least 2.5 inches, preferably at least 4 inches, more preferably at least 7 inches, and even more preferably approximately 9 inches. In another embodiment for repairing a defect using a laparoscopic procedure, the length of the tether is at least 10 inches, preferably at least 12 inches, more preferably at least 14 inches, and even more preferably approximately 15 inches for use with a cannula having a length of 6-6.5 inches. It is to be appreciated that the disclosed tether lengths are exemplary and that any suitable tether length may be employed for a particular repair.

In some procedures, it may be difficult for a surgeon to determine when the patch 22 has been inserted a required distance into the body to be positioned at the repair site. In one illustrative embodiment, the tether 24 may include an indicator 60 disposed a predetermined distance from the patch. The appearance or disappearance of the indicator 60 proximate the edge of the wound or the proximal end of a cannula acknowledges that the patch 22 has been inserted a desired depth within the body cavity of the patient without direct visualization of the patch, such as with a camera. For example, when the indicator 60 is located proximate the proximal end of the cannula during laparoscopic insertion of the patch, the indicator may reveal that the patch has passed through the cannula and is deployed at the defect site. As a representative example, for a cannula having a length of approximately 6-6.5 inches, the indicator may be located approximately 7.5-8.5 inches from the patch. However, it should be appreciated that the invention is not limited in this respect and that the prosthesis 20 need not employ an indicator 60.

In one illustrative embodiment, the indicator 60 includes a series of stitches formed with a thread having a contrasting color as compared to the material of the tether. For example, the thread of the indicator may be colored blue and the tether may be colored white. It is to be appreciated that other suitable indicators formed in other suitable manners may be employed. For example, contrasting ink or dyes may be applied to the tether, or the material of the tether may be treated to change its appearance, texture, or shape, such as with a heat seal or indentation, to indicate the implantation depth of the patch. One or more indicators 60 may be disposed on the tether at multiple locations to indicate various desired or optional implantation locations of the patch. For example, two or more indicators may be located on the tether for use with cannulas of differing lengths. The indicator 60 may also numerically indicate the depth of the implanted patch with a measured and/or numbered indicator or ruler disposed on the tether. The indicator may be preformed on the tether, or alternatively, may be formed on the tether by the surgeon at the desired implantation depth of the patch for a particular procedure.

As illustrated, the tether 24 has a strap-like configuration having a cross section with a width that is greater than its thickness. The strap configuration may distribute forces over a larger region of the patch as compared to a suture-like tether. The strap may also present a relatively large surface area that may facilitate the repair, such as by enhancing tissue integration to the tether, if desired. Although the tether 24 is shown as having a constant width along its length, the invention is not limited in this respect, and other strap configurations may be suitable. For example, the width of the strap may vary along the length such that the strap is wider at its distal end and narrower at its proximal end. It is to be appreciated, however, that the tether is not limited to a strap configuration as the prosthesis may employ any suitable tether configuration apparent to one of skill.

The tether may be joined to the patch 22 using any suitable fastener or attachment arrangement. In the illustrative embodiment, the tether 24 includes a base or foot that is stitched to the patch 22 along a stitch line 23. It is to be appreciated that other suitable attachment methods may be employed including, but not limited to, bonding, adhesives and other attachment methods apparent to one of skill in the art. Alternatively, the tether may be integrally formed with the patch, such as by forming the tether and a portion of the patch from the same piece of material.

The strap configuration may also reduce potential tearing of the tissue and muscle at the edge of the defect 28 by the tether 24 during and after the repair procedure, particularly when compared to a suture-like tether. In this regard, the large surface area of the tether may resist tearing of the tissue and muscle proximate the defect when the tether is pulled during the procedure. In addition, the large width of the tether may resist tearing through the tissue and muscle proximate the defect during the healing process.

The tether is preferably flexible along its length from its distal end 36 to its proximal end 40 to facilitate repair of a defect. To facilitate repair of a defect, the tether may be formed of a repair fabric that permits or is otherwise susceptible to tissue or muscle integration. In one embodiment, the tether may include a plurality of interstices or openings which allow sufficient tissue or muscle wall ingrowth to secure each tether to host tissue or muscle after implantation. However, the invention is not limited in this respect and the tether may be formed of a material or otherwise configured to enhance tissue integration, inhibit adhesion, or a combination of both, as desired.

The patch may be anchored over to repair the tissue or muscle wall defect by attaching the tether 24 to or proximate the edge of the tissue or muscle defect. The tether may be attached to tissue, skin, and/or muscle using any suitable attachment methods apparent to one of skill in the art, such as sutures, tacks, and/or staples. In this manner, the defect may be repaired in a tension free manner since it is not necessary to reapproximate the tissue at the defect and/or to attach the patch directly to tissue or muscle in the region of the defect.

The patch 22 may be configured to have any suitable shape or size that is conducive to facilitating the correction or repair of a particular defect. In the embodiment shown in FIG. 1, the patch 22 has a relatively flat configuration. However, the patch need not be flat, and convex, concave, convex/concave, and more complex three-dimensional shapes also are contemplated, as noted above. The patch may be pliable to facilitate manipulation and/or reduction of the patch during delivery to the defect and/or to conform the patch to the anatomical site of interest. As illustrated, the patch has a generally circular shape. Examples of other shapes include, but are not limited to, oval, square, rectangular, and irregular configurations. The patch 22 may be sized to cover part or, preferably, all of the defect. In one embodiment, the patch 22 is sized to extend slightly beyond the edge margins of the tissue or muscle wall defect. It should be understood, however, that any suitable size and shape may be employed for the patch.

The patch 22 may include one or more layers of repair fabric that may promote tissue ingrowth to the patch, inhibit adhesions to the patch, or a combination of both. In one illustrative embodiment, the patch includes an ingrowth layer 64 having a plurality of interstices or openings which allow sufficient tissue or muscle ingrowth to integrate the prosthesis with the host tissue or muscle after implantation. Preferably, the ingrowth layer is formed of the same tissue infiltratable material used for the tether. However, the invention is not limited in this respect, as the ingrowth layer may be formed of any suitable biologically compatible material apparent to one of skill.

To inhibit collapse of the patch 22 into the defect 28 when force is applied to the tether, and/or to help deploy the patch into a planar configuration, it may be desirable to employ a patch that is sufficiently rigid so that it can be easily and effectively manipulated and positioned in the desired area, yet sufficiently flexible so that the patch is adequately tolerated by both the physician implanting the patch and the patient receiving the patch. In one illustrative embodiment as shown in FIG. 1, to balance the stiffness and flexibility characteristics, the prosthesis 21 includes a resilient support member 98 to reinforce portions of the patch 22 and to urge the patch to a planar configuration. The support member 98 may be coupled to the patch 22 in any suitable manner, as the present invention is not limited in this respect. Suitable attachment methods include, but are not limited to, stitching, bonding, adhesive, and integral formation with the repair fabric of the patch, as will be discussed further below.

The resilient support member 98 contributes to the stability of the patch 22, allowing it to deploy into and remain in a desired shape. For example, the support member may aid in returning the patch to a substantially unfurled or expanded configuration after the folded up or otherwise reduced implant has been delivered through the cannula. This stability facilitates deployment and placement of the patch by making it easy to handle. Also, this stability minimizes the tendency of the patch to sag, fold, bend, collapse, or otherwise be dislocated. Difficulty in handling, dislocation or bending could require additional operative procedures and/or additional anchoring during implantation.

As indicated above, a prosthesis for repairing or augmenting soft tissue and muscle wall defects, such as an umbilical hernia or a trocar wound created in the abdominal wall of a patient during a laparoscopic surgery, may include a body portion of any suitable configuration and one or more tethers extending from the body portion.

In another illustrative embodiment shown in FIGS. 2-7, the prosthesis 20 includes a patch 22 for covering at least a portion of the defect, and a pair of tethers 24, 26 extending from the patch to facilitate positioning and/or anchoring of the patch at the defect site. As shown, the tethers extend from a surface 34 of the patch that is to face the defect 28 when the patch 22 is implanted in the patient's body so that the tethers may be routed through the defect. Each tether is configured with a length that is sufficient to extend through the defect to a region that is accessible from outside the body, as described above. Additionally, each tether has a strap-like configuration similar to the embodiment of FIG. 1. It is to be understood, however, that the tethers may be configured with any suitable size and shape apparent to one of skill.

As illustrated in the embodiment of FIGS. 2-7, the tethers 24, 26 extend from the patch at spaced apart junctions 44, 46 between the tethers and the patch 22. In this manner, the spaced junctions transfer forces from the tethers to different portions of the patch, rather than applying the forces in a more concentrated region. This arrangement may enhance force distribution across the patch so as to reduce the potential for collapsing the patch into the defect and pulling the patch through the defect. The spaced junctions between the tethers and the patch may also facilitate positioning and manipulation of the patch. In this regard, tension may be applied to one or the other of the tethers to guide or direct the patch, similar to reins. However, it should be appreciated that the invention is not limited in this respect, and that the tethers may be joined or attached to the patch in other suitable locations.

To secure the patch 22 to repair the tissue or muscle wall defect without reapproximating the tissue or muscle surrounding the defect, the tethers 24, 26 may be attached to opposite edges of the tissue or muscle defect. In this manner, forces applied to the patch 22 by the tethers are relatively balanced to the body of the patch, and thus, facilitate maintenance of the patch in its desired implantation position. It is to be appreciated that other suitable attachment arrangements of the tethers may be used as would be apparent to one of skill. For example, the tethers may each be attached to the same side of the defect. As described above, the tethers may be attached to the tissue, skin, and/or muscle using suitable attachments known in the art, such as sutures 54, tacks, and/or staples. In this manner, the defect may be repaired in a tension free manner since it is not necessary to reapproximate the tissue at the defect, and the patch is anchored over the defect with the tethers secured to the opposing edges of the defect.

In certain repairs, it may be desirable to vary forces at different regions of the patch. In one embodiment, the tethers 24, 26 may be joined to the patch 22 at junctures 44, 46 which are not symmetric about the center of the patch. In another embodiment, one strap 24 may be longer than the other strap 26 after the straps are attached to secure the patch 22. In this manner, extending the tethers from different locations of the prosthesis and/or employing straps of differing lengths or sizes may act to spread the forces to the patch in a predetermined manner.

As illustrated, the prosthesis may include an indicator 60, as described above, as an aid for a surgeon in determining when the patch 22 has been inserted a sufficient distance within the patient. The indicator 60 may be provided on either one or both tethers 24, 26. In the illustrative embodiment of FIGS. 2-7, the indicator includes a thread that attaches the tethers to each other.

In certain procedures, such as a laparoscopic procedure, the prosthesis 20 may be used to repair a fairly small trocar wound that itself may be too narrow for delivery of the patch 22. One approach is to deliver the patch 22 and the attached tethers 24, 26 to the wound site 28 through a separate cannula or entry wound that is large enough to accommodate transport of the patch. In this manner, the patch may be deployed at or near the slender trocar wound and at least a portion of the tethers are accessible for the surgeon to retrieve and extract the tethers through the defect 28. The tethers may then be pulled, pushed, or otherwise manipulated. In this manner, the indicator of a contrasting color may help the surgeon locate the tethers inside the body cavity to ease the extraction of the tethers through the defect to be repaired.

In the illustrative embodiment of FIGS. 2-7, the prosthesis 20 includes a patch 22 which is relatively flat and circular. However, the patch need not be flat and/or circular, and three dimensional and other shapes may be suitable, as discussed above.

The patch may include an ingrowth layer 64 of tissue infiltratable material to enhance the repair of the defect. The ingrowth layer includes at least one layer of repair fabric that permits or is otherwise susceptible to tissue or muscle ingrowth. In the embodiment of FIGS. 2-7, the ingrowth layer 64 includes first and second layers 66, 68. Each layer 66, 68 is formed of a biologically compatible, flexible repair material that includes a plurality of interstices or openings which allow sufficient tissue or muscle ingrowth to integrate the prosthesis with host tissue or muscle after implantation. Multiple layers of tissue infiltratable fabric may enhance the strength of the patch and/or the amount of tissue ingrowth to the patch. Preferably, the first and second layers are formed of the same tissue infiltratable material as that of the tethers. However, the invention is not limited in this respect, and either one or both layers may be formed of any biologically compatible material, suitable for repairing a tissue or muscle wall defect as would be apparent to one of skill.

In one embodiment, the tethers 24, 26 and ingrowth layers 64, 66, 68 of the prostheses 20, 21 are formed from a sheet of knitted polypropylene monofilament mesh fabric such as BARD MESH available from C. R. Bard, Inc. When implanted, the polypropylene mesh promotes rapid tissue or muscle ingrowth into and around the mesh structure. Alternatively, other surgical materials which are suitable for tissue or muscle reinforcement and defect correction may be utilized including SOFT TISSUE PATCH (microporous ePTFE—available from W. L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Absorbable materials, including polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the tether mesh material. Alternatively, the tether may be formed of a monofilament of any of the above materials or a suture material, which may be absorbable or non-absorbable. It is preferable that the material of the tether have a tensile strength of approximately 3 lb. force or more.

To ensure adequate tissue ingrowth to the patch occurs, the layers 66, 68 may be attached or joined in a way that would permit tissue to grow into the pores of the first and second layers and provide a strong bond between the surrounding muscle or tissue in the first and second layers. In one embodiment, the first and second layers are connected with stitches 70, 72 proximate the periphery 74, 76 of each layer.

It should be appreciated that the invention is not limited to any particular attachment method, as the first and second layers 66, 68 may be attached using other suitable techniques. For example, the layers may be bonded together by melting the layers at specific locations or in a specific pattern; sonic, induction, vibration, or infrared/laser welding the layers; or using a suitable bonding agent. The point or points of attachment may comprise any suitable pattern, such as a spiral pattern, a serpentine pattern, or a grid-like pattern of dots or beads, that maintains a sufficient quantity of open or non-impregnated interstices for tissue or muscle infiltration.

To aid in deploying and/or positioning the patch during implantation, the patch 22 may include a pocket 78. In this manner, a physician may use the pocket 78 to deploy or position the patch in the desired area or implantation location. In the embodiment shown in FIGS. 2-7, the first and second layers 66, 68 are attached in a manner to form a pocket 78 therebetween. However, it should be appreciated that the invention is not limited in this respect and that a pocket need not be employed or that other suitable pockets formed in other suitable manners may be employed. For example, a pocket may be formed from an additional layer of material or portion thereof attached to the first layer 66 and/or the second layer 68.

To gain access to the interior of the pocket 78, the patch 22 includes an access opening 80. In one embodiment, the opening 80 includes a transverse cut or slit formed in the second layer 68 which may follow a diameter of the patch. It should be recognized that the access opening may be oriented in any position and located across any portion of the patch as may be suitable for the repair procedure.

To position and/or deploy the patch, the surgeon may insert one or more fingers (or suitable surgical instrument) through the access opening and into the pocket to manipulate the patch into place. In one embodiment, the pocket 78 is sized to accept at least one finger of the surgeon's hand or a tool for positioning the implant, although other suitably sized pockets may be employed as the present invention is not limited in this respect. Further, the pocket may be formed as multiple pockets so that one or more fingers or instruments may be inserted into individual sections. In the embodiment shown in FIGS. 2-7, the pocket 78 includes a first side pocket 82 and a second side pocket 84 on opposing sides 86, 88 of the opening. However, it should be appreciated that the invention is not limited in this respect and that only a single central or off-set pocket may be employed.

As illustrated, the tethers 24, 26 are attached to the second layer of fabric 68, which is itself attached to the first layer of fabric 66 at its periphery 74, 76. As force is applied to the tethers, the second layer of fabric will tend to billow from the first layer of fabric. The forces on the tethers are transmitted through the second layer of fabric and to the first layer of fabric at the peripheral attachment of the first and second layers of repair material. In this manner, the attachment of the tethers to the second layer may act to inhibit collapse of the prosthesis by spreading forces to the periphery of the patch.

The tethers 24, 26 may be attached to the second layer of fabric 26 on opposing sides 86, 88 of the access opening 80, as shown in FIGS. 2-7. As force is applied to the tethers, the billowing second layer 68 may open and expand the access opening 80 to the pocket 78. The gaping access opening spreads or spaces apart the junctions 44, 46 of the tethers 24, 26 and the patch. In this manner, the temporary spacing of the junctions 44, 46 spreads the forces on the tethers away from the center and towards the periphery of the patch.

To further enlarge the access opening 80 during the repair procedure, the surgeon may pull the tethers 24, 26 away from each other. In this manner, the access opening can be drawn open, allowing less restricted access to the pocket 78 to position or manipulate the patch. The exposed access opening between the tethers and through the defect may also facilitate access to the broad surface 30, 32 of the tethers 24, 26 when attaching the tethers to the edges of the defect. Additionally or alternatively, sutures, staples, or tacks (not shown) may be placed through the patch, if desired, into surrounding tissue and/or muscle to secure the prosthesis.

To facilitate the fabrication of the prosthesis, the tethers may be integrally formed with the second fabric layer. In one illustrative embodiment shown in FIG. 6, an elongated piece of repair fabric includes a pair of layer portions 68A, 68B disposed at opposite ends of an elongated strap. The layer portions may be configured so as to form a desired shape of the second fabric layer. As shown, each layer portion 68A, 68B may be configured with a semi-circular shape to form a circular second layer when combined. The strap may be folded in half along a fold line 96 to form the first and second tethers 24, 26 between the fold line 96 and the layer portions. Each half of the second layer of fabric may be folded out to form the generally planar second layer 68 at the distal end of the tethers. In this manner, the access opening 80 is formed between the two tethers and each half of the second layer of fabric.

As illustrated, the proximal ends 40, 42 of the tethers are joined to form a loop or handle that may be grasped and pulled by the surgeon. If desired, the proximal ends of the tethers may be separated before, during, or after implantation of the prosthesis. It should also be appreciated that the tethers 24, 26 may be separately attached to the patch in other suitable locations. Additionally, the tethers may be joined to any one or all layers of the patch.

To inhibit collapse of the patch 22 into the defect 28 when force is applied to the tethers 24, 26, and/or to help deploy the patch into a planar configuration, a resilient support member may be disposed on the patch. In one embodiment, the resilient support member 98 includes a substantially continuous loop or ring positioned adjacent the outer margin 100 of the patch 22. In the embodiment shown in FIGS. 2-7, the support member 98 is spaced inwardly from the outer peripheral edges 74, 76 of the layers of fabric 66, 68. However, it should be appreciated that the present invention is not limited in this respect, as the support member may be disposed at the peripheral edge and/or at discrete locations throughout the body of the patch.

In the embodiment shown, the support member 98 includes a monofilament of a desired thickness and cross-sectional shape to provide a desired degree of resilience or rigidity. It should be appreciated that the support member may have any cross-sectional shape, such as circular, square, rectangular, triangular, elliptical, etc. The support member may be configured on the patch in any pattern, such as a spiral pattern, a square pattern, an elliptical pattern, a circular pattern, crisscross pattern or the like.

The stiffness or rigidity of the support member may be varied depending on the size of the patch. For example, the cross-sectional diameter and/or the spring constant of the material of the monofilment thread may be varied in a manner to provide a desired stiffness. In one embodiment, for a patch 22 having a diameter of approximately 1.75 inches, the support member 98 is formed from a segment of 0.03 inch polyethylene terephthalate (PET) monofilament thread having a length of approximately 3.375 inches. In this manner, the monofilament thread may be formed into a loop having a diameter of approximately 1.1 inches. In another embodiment for a patch having a diameter of approximately 2.5 inches, the support member may be formed from a segment of 0.030 inch PET monofilament thread having a length of 5.94 inches. In this manner, the monofilament thread may be formed into a loop having a diameter of approximately 1.81 inches. However, it should be appreciated that the invention is not limited in this respect and that the support member may be made of any suitable material including nylon, polypropylene, and polyester and having any suitable diameter or cross-section.

The support member 98 may be disposed on the patch 22 in any suitable manner as the present invention is not limited in this respect. In one embodiment, as shown in FIGS. 2-7, the resilient support member 98 is sandwiched between the first and second layers of repair fabric 66, 68 and may or may not be physically attached thereto. The support member may be tightly or loosely held within a channel 102 between the first and second layers 66, 68 and formed by a pair of seams joining the first and second layers. In the illustrative embodiment, the channel 102 is formed by a pair of seams 70, 72 that follow the contour of the periphery 74, 76 of the layers. The seams may be formed by a series of stitches extending along the outside and inside edge of the resilient support member 98 to keep it from moving with respect to the first and second layers. Because of the rigidity of the resilient support member, one seam extending along one side of the support member may be sufficient.

Alternatively, rather than being sandwiched between the first and second layers 66, 68, the support member 98 may overlie or underlie the ingrowth layer 64 and may be attached, regardless of location, with stitches or a bonding agent, or fused with ultrasonic, induction, vibration, infrared/laser welding and the like. Alternatively, the support member may be woven through at least one of the layers or integrally formed with one or both layers as the layer itself is being made.

Although the support member 98 is described as being formed of a monofilament, other suitable constructions may be employed. For example, the support member may be molded elements that are subsequently attached to the patch or molded onto the patch. As another example, the support member may be formed from the ingrowth layer 64. In this respect, the support member may be formed by melting a portion of the ingrowth layer in any desired shape. The support member may be formed by applying heat to the ingrowth layer at a temperature range of approximately 320° F. to 400° F. for a period of approximately 3-5 seconds. In another example, the support member may be formed by multiple stitches passing through one or both layers, such as, for example, an embroidered section. Alternatively, the support member may be formed by altering the weave pattern in a zone of desired reinforcement. In this manner, the area of the ingrowth layer where tissue ingrowth is desired may be formed with a relatively loose open weave, whereas the area or zone of reinforcement may be formed with a relatively tight weave, to provide the desired rigidity. Other suitable methods or mechanisms to form the support members may be employed, as the present invention is not limited in this respect. Although some embodiments described above include support members, the present invention is also not limited in this respect.

In certain procedures, such as in the repair of trocar wounds in the chest or abdominal wall or groin region, it may be desired to limit or prevent contact between the ingrowth layer 64 and certain tissue, muscle or organs. Such contact could potentially lead to undesirable postoperative adhesions between the ingrowth layer and the surrounding tissue, muscle or organ and/or erosion of the ingrowth layer into the neighboring anatomy or other injury. To minimize or eliminate the incidence of postoperative adhesions to selected portions of the patch 22, or other trauma, the prosthesis 20 may include an adhesion resistant barrier overlying at least a portion, and preferably all, of one side of the ingrowth layer.

In one illustrative embodiment as shown in FIGS. 2-7, a barrier layer 104 is attached to the side 106 of the patch 22 adjacent the first layer 66 that is to face away from the defect 28. The patch 22 is to be positioned in the patient such that the barrier layer 104 faces the region of potential undesired adhesion, such as the abdominal viscera (e.g., intestines) or the thoracic viscera (e.g., heart or lungs). The barrier layer is formed of a material and/or with a structure that does not substantially stimulate and, in certain embodiments, may resist tissue, muscle or organ ingrowth and adhesion formation when implanted, thereby reducing the incidence of undesired postoperative adhesions between the ingrowth layer 64 and adjacent tissue, muscle or organs.

In one embodiment, the barrier layer 104 is formed from a sheet of expanded polytetrafluoroethylene (ePTFE) having fibril lengths—also referred to as pore size or internodal distance—that will not permit significant tissue ingrowth. In one embodiment, the fibril lengths of the ePTFE are less than 5 microns. In another embodiment, the fibril lengths of the ePTFE are less than 1 micron and in still another embodiment, the fibril lengths are less than 0.5 microns. Examples of other suitable materials for forming the barrier layer 104 include FLUORO-TEX Pericardial and Peritoneum Surgical Membrane and FLUORO-TEX Dura Substitute available from C. R. Bard and PRECLUDE Pericardial Membrane, PRECLUDE Peritoneal Membrane and PRECLUDE Dura Substitute membrane available from W. L. Gore & Associates, Inc. A representative and non-limiting sampling of other suitable micro to non-porous materials includes silicone elastomer, such as SILASTIC Rx Medical Grade Sheeting (Platinum Cured) distributed by Dow Corning Corporation, and microporous polypropylene sheeting (available from Celgard, Inc.) and film. Autogenous, heterogenous and xenogeneic tissue also are contemplated including, for example, pericardium and small intestine submucosa. Absorbable materials, such as SEPRAFILM available from Genzyme Corporation and oxidized, regenerated cellulose (Intercede (TC7)) may be employed for some applications. It is to be appreciated that other suitable biocompatible adhesion resistant materials also may be used.

To permit and facilitate tissue or muscle growth into the first layer of repair material 66, the barrier layer 104 is preferably attached to the first layer 66 in a way that would permit tissue to grow into the pores of the first layer and provide a strong bond between the surrounding muscle or tissue and the first layer. In one embodiment, the barrier layer is attached to the ingrowth layer with stitches. Although the attachment is shown to include concentric patterns of stitch lines, any suitable pattern may be employed so as to minimize separation of the ingrowth layer 64 and the barrier layer 104, to minimize the number of stitching holes through the barrier layer and to facilitate the manufacturing process. It should also be appreciated that the barrier layer may be attached using other suitable materials, techniques and/or patterns. For example, the barrier layer may be bonded to the ingrowth layer by heating the layers, by welding the layers, or using a suitable bonding agent. Any suitable pattern, such as a spiral pattern, a serpentine pattern, or a grid-like pattern of dots or beads may be used provided there is a sufficient quantity of open or non-impregnated interstices maintained in at least one layer for tissue and muscle infiltration.

In one embodiment, as shown in FIGS. 2-7, the first and second layers of repair fabric 66, 68 are attached together and to the barrier layer at discrete attachment lines using stitches, which allow sufficient tissue infiltration to the ingrowth layer, while providing a connection between the first and second layers and the barrier layer. In addition, some or all of the stitches may be used to secure only the first and second layers of repair fabric. In the embodiment shown, the first or outer line of stitches 72 attach only the first and second layers of repair fabric 66, 68, whereas the second or inner line of stitches 74, forming the channel 102 for the resilient support member 98, attach the first and second layers of repair fabric 66, 68 with the barrier layer 104. In this manner, the number of holes created by stitches in the barrier layer 104 are decreased to minimize the leakage of gases, such as those to insufflate the body cavity during a laparoscopic procedure.

To further minimize any undesired adhesions, the stitches 74 may be formed from a non-porous, adhesion resistant material. In one embodiment, the stitches 74 are formed with a suitable polytetrafluoroethylene (PTFE) monofilament. The PTFE stitches may provide a softer, more flexible prosthesis that is easier to manipulate as compared to a prosthesis using other stitch materials, such as polypropylene monofilament. PTFE monofilament also facilitates the manufacturing process due to the low friction characteristics of the material. Nevertheless, it should be understood that any suitable material, such as polypropylene monofilament, may be employed for the stitches. For example, because some of the stitch lines 72 do not pass through the barrier layer, or where no barrier layer is employed, materials other than an adhesion resistant material may be employed. For ease of manufacturing however, typically, all stitches 72, 74 are formed of the same material, although the invention is not limited in this respect.

The layers 66, 68, 104 may be stitched using a typical sewing stitch formed by a sewing machine using a bobbin and sewing thread. Preferably, the barrier layer 104 is positioned on the ingrowth layer 64 to face the sewing needle so that the locking position of each stitch (i.e. the bobbin) is formed on the ingrowth side 34 of the patch 22 rather than on the barrier side 106 to reduce the incidence of localized adhesions with tissue, muscle or organs. The stitches 72, 74 may be formed using a #10 ball-tipped needle to reduce the potential incidence of ingrowth through the stitch holes. The sheets of ingrowth material 66, 68, with or without the barrier layer 104, may be held by a frame during the sewing procedure on a computer controlled table that has been programmed with the desired stitch pattern.

While the barrier layer 104 preferably covers the entire surface of one side 106 of the ingrowth layer 64, the barrier layer may be configured to cover only selected portions of one side of the patch to enhance ingrowth from both sides in those portions free of the barrier layer. Similarly, the patch may be configured such that the barrier layer covers the entire surface on one side 106 of the patch and covers one or more portions of the other side 34 of the patch.

In some instances, it may be desirable to isolate the outer peripheral edge 110 of the patch 22 from adjacent tissue, muscle or organs. In one embodiment, a peripheral barrier 108 extends completely about the outer peripheral edge 110 of the patch to inhibit adhesions thereto. It is to be understood, however, that the peripheral barrier may be configured to cover only those selected portions of the outer peripheral edge of the prosthesis where protection from the formation of postoperative adhesions is desired.

The peripheral barrier 108 may be formed integrally with either the ingrowth layer 64 or the barrier layer 104. Alternatively, the peripheral barrier may be formed by a separate component that is attached to or incorporated into the outer peripheral edge of the prosthesis. In one illustrative embodiment, the peripheral barrier is formed from a portion of the ingrowth layer. In particular, the ingrowth layer may be altered so as to substantially eliminate the tissue infiltratable interstices or openings along its outer margin, thereby creating a peripheral barrier.

In one embodiment, as shown in FIGS. 2-7, the peripheral edges 72, 74 of the layers of repair fabric 66, 68 are melted to seal the material and form an outer peripheral barrier 108. The barrier layer 104 may be configured, such as with submicronal sized pores, so that a portion of the melted material of repair layers become fused to the barrier layer. The peripheral edge 110 of the patch may be melted using any suitable process. In one embodiment, the peripheral edge may be melted by heat sealing the layers of repair fabric 66, 68. In the exemplary embodiment, the peripheral barrier 108 is formed by melting a ring of polypropylene mesh fabric 66, 68 to the ePTFE barrier layer 104 in a shape that approximates the desired configuration of the patch 22. This may be accomplished by overlying oversized sheets of the mesh fabric and ePTFE material in a fixture and heat sealing the layers using a heated die configured with the desired shape of the prosthesis. The melted ring may be formed by applying heat to the fabric at a temperature range of approximately 320° F. to 440° F. for a period of approximately 3 to 5 seconds. The temperature chosen typically should be below the sintering temperature of the ePTFE barrier layer. Other sealing techniques may be used, such as ultrasonic, induction, vibration, infrared/laser welding and the like, as the present invention is not limited in this respect. Once fused, the ingrowth layer is stitched to the barrier layer, as described above, and subsequently die cut flush along a portion of the ring to complete the patch with a peripheral barrier.

In an exemplary embodiment for the prosthesis of FIG. 2-7, the first and second layers 66, 68 and the two tethers 24, 26 are each formed from an approximately 0.027 inch thick sheet of BARD MESH knitted from polypropylene monofilament with a diameter of approximately 0.006 inches. Each tether is integrally formed with the second layer of repair fabric from a single sheet of BARD MESH. The access opening 80 in the second layer and between the tethers extends across the diameter of the second layer and between the stitch lines of the second or inner stitch line 72. The surface barrier 104 is formed from an approximately 0.006 to 0.008 inch thick sheet of ePTFE. The surface barrier and the first and second layers are attached with approximately 3 mm to 4 mm long stitches formed of a 0.008 inch to 0.012 inch diameter PTFE monofilament. The first or outer stitch line 70 attaches only the first and second layers and is placed approximately 0.5 cm in from the peripheral edge of the layers of repair fabric. The second or inner stitch line 72 attaching the first and second layers to the surface barrier is placed approximately 1 cm in from the peripheral edge of the layers and the surface barrier. The resilient support member 98 is a continuous loop formed from an approximately 0.03-0.042 inch diameter PET monofilament. The resilient support member is held in the 0.5 cm channel 102 formed between the first and second stitch lines 72, 74. The outer 0.5 cm of the peripheral margin 100 of the first and second layers are heat sealed to the surface barrier to supplement attachment of the first layer, the second layer, and the surface barrier. Each tether is approximately 0.62 inches wide and has a length of approximately 15 inches. The patch location indicator 60 includes a stitch line formed from approximately 0.0068 inch diameter blue unannealed polypropylene monofilament thread that is colored blue. The indicator stitch line is located approximately 8 inches from the distal ends 36, 38 of the tethers, and attaches the two tethers to each other to form a loop.

Figure 8:
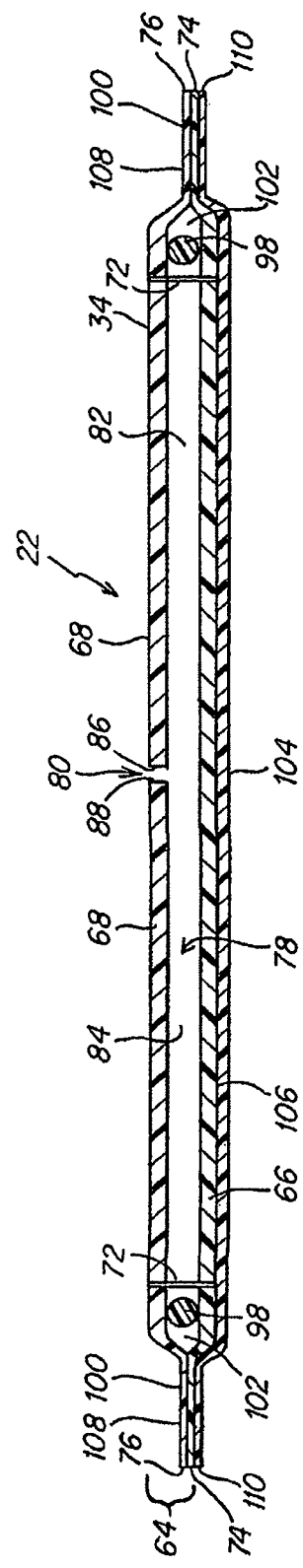
FIG. 8 is a cross-sectional view, similar to that of FIG. 4, in accordance with a further illustrative embodiment of the present invention.
Figure 7:
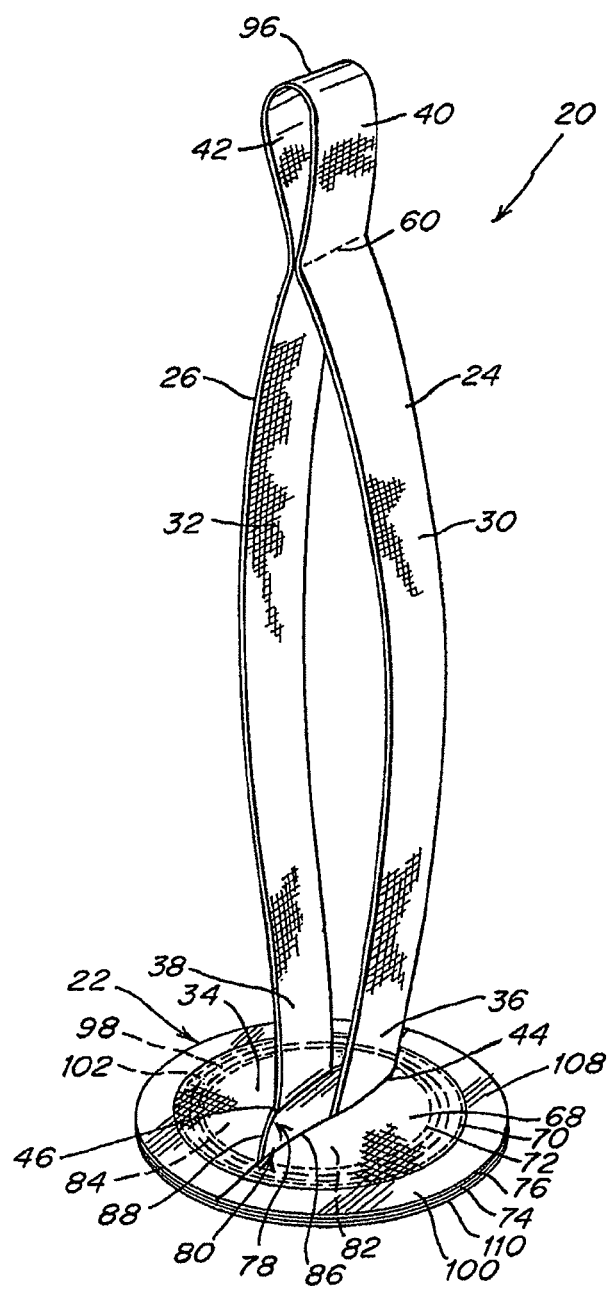
FIG. 7 is a top perspective view of the prosthesis of FIG. 2, with the access opening exposed to the pocket.

In an illustrative embodiment shown in FIG. 8, the peripheral margins 100 of the first layer 66, the second layer 68, and the surface barrier 104 are heat melded to seal the outer periphery of the layers and form the peripheral edge barrier 108. The channel 102 for the support member 98 is formed between the heat seal 108 and a single line of stitches 74 attaching the first and second layers to the surface barrier. In this manner, the number of stitch holes in the patch are decreased.

In some repair procedures, it may be desired to employ a tethered prosthesis in conjunction with one or more other prostheses. In one illustrative embodiment shown in FIG. 9, the prosthesis of FIGS. 2-7 may be employed in conjunction with an overlay prosthesis 116 for repairing an inguinal hernia. The overlay prosthesis 116 is sized and shaped to overlay the defect such that the defect is sandwiched between the tethered prosthesis 20 and the overlay prosthesis 116. To repair the defect and to attach the prosthesis 20 to the overlay prosthesis 116, the tethers 24, 26 of the prosthesis 20 may be routed through the defect and threaded through tether openings 118, 120 in the overlay patch 116. In this manner, the tethers are slidably attached to the onlay patch. However, the invention is not limited in this respect and the tethers may be joined or attached to the onlay patch in any suitable manner, including sutures, melding, and bonding.

Tension may be applied to the tethers to draw the patch 22 against the underside of the defect from a remote location. The onlay patch 116 may also be positioned on the top side of the defect by pulling the tethers 24, 26 in opposing directions to slide the onlay patch down the tethers and more proximate to the defect below the onlay patch. The onlay patch may be attached to tissue, muscle or other anatomy proximate the defect as would be apparent to one of skill in the art. The tethers may be attached directly to the onlay patch or to tissue, muscle, or other anatomy proximate the defect, as desired by the surgeon. The excess tether may then be removed and disposed.

Figure 9:
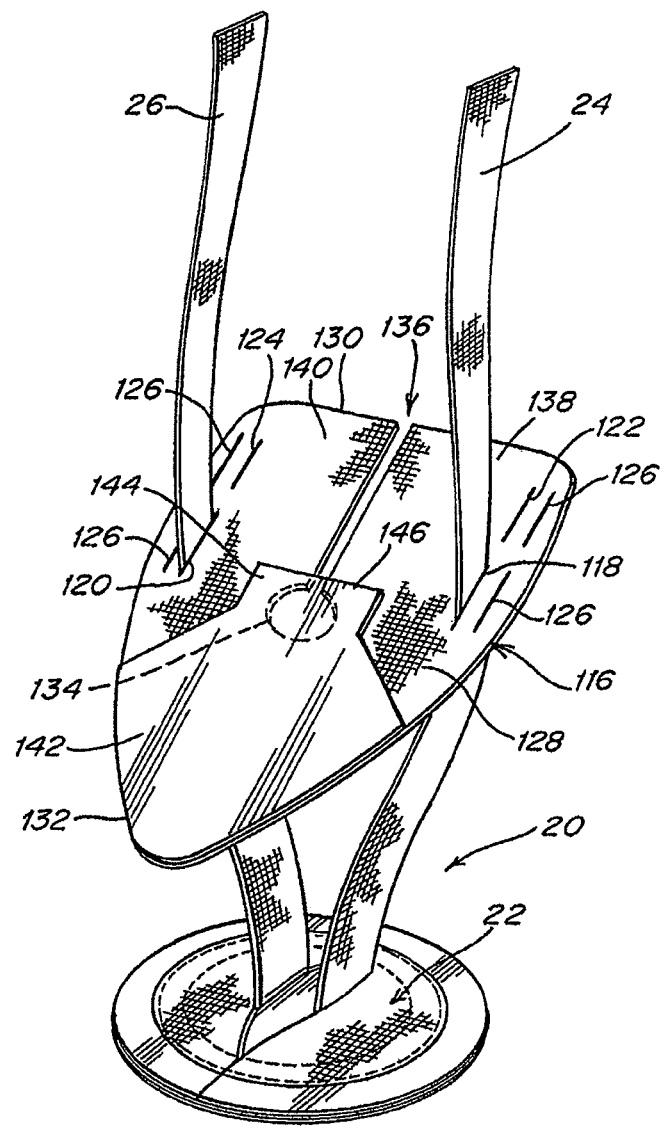
FIG. 9 is a top perspective view of the implantable prosthesis of FIG. 2 used in conjunction with an onlay prosthesis in accordance with another illustrative embodiment of the present invention.

In the embodiment shown in FIG. 9, the tether openings 118, 120 are elongated cuts or slits formed in the fabric of the onlay patch 116. The slits 118, 120 may extend generally parallel to the periphery of the onlay patch. However, it should be recognized that the tether openings 118, 120 may be oriented in any manner in relation to the periphery and/or body of the onlay patch, and may have any shape to accommodate the tethers and/or anatomy proximate the defect.

One or more tether openings may be provided in the onlay patch to provide various configurations for the attachment between the tethers and the onlay patch. In the illustrative embodiment, a first pair of tether openings 118, 120 are provided in the onlay patch 116 to repair a direct inguinal hernia, and a second pair of tether openings 122, 124 are provided in the onlay patch to repair an indirect hernia. However, it should be appreciated that the invention is not limited in this respect, and that any number of tether openings may be placed in any suitable configuration for repairing the tissue or muscle wall defect.

The onlay patch may also include one or more tether holes for securing the tethers to the patch. As illustrated, a tether hole 126 is provided in the onlay patch 116 adjacent each of the tether holes 118, 120, 122, 124. The tethers 24, 26 may be inserted into the onlay patch through either set of tether holes 118, 120 or 122, 124. To facilitate anchoring the tethers, the tethers may be woven through the onlay patch by threading the tethers through adjacent tether holes 126.

The onlay patch may be formed of a biologically compatible, flexible layer of repair fabric suitable for reinforcing tissue or muscle wall and closing anatomical defects. In one illustrative embodiment, the onlay patch is formed of a layer of tissue infiltratable repair fabric 128 in a generally D shape, with a lateral edge 130 and a rounded medial edge 132. A keyhole opening 134 may be formed at the end of a slit 136 that extends inwardly from the lateral edge 130 of the onlay patch to create a pair of tails 138, 140. The pair of tails may be separated to receive a tube-like structure, such as the spermatic cord in an inguinal hernia repair. However, it should be recognized that the onlay patch may be configured to have any suitable shape that is conducive to facilitating repair of a particular defect.

To isolate portions of the fabric 128 from the adjacent tube-like structure, portions of the fabric 128 may be covered with a surface barrier 142. In the illustrative embodiment, the surface barrier extends inwardly from the medial edge of the fabric 128 to the keyhole opening 134. To further protect the tube-like structure from the edges of the fabric at the keyhole opening, the onlay patch 116 may also include an edge barrier 144. The edge barrier 144 may be configured as a flap 146 of the surface barrier which may then be wrapped around the tube-like structure as it passes through the keyhole opening. One example of an onlay patch 116 is disclosed in U.S. Pat. No. 6,258,124 to Darois et al., assigned to C. R. Bard, Inc. However, the invention is not limited in this respect and the prosthesis 20 may be used without an onlay patch or with an onlay patch having any suitable configuration.

It is to be understood that the above embodiments are exemplary and any suitable patch and tether configuration may be implemented to repair a tissue or muscle wall defect.

One embodiment of a repair procedure to implant the prosthesis to repair a trocar wound will now be described with reference to FIGS. 10-13. The defect 28 is identified by the placement of the cannula 58 during a laparoscopic procedure. However, it is to be appreciated that the invention is not limited in this respect, and a cannula 58 need not be employed to deliver the patch 22 and the opening of the defect need not be located through the skin of the patient.

Figure 10:
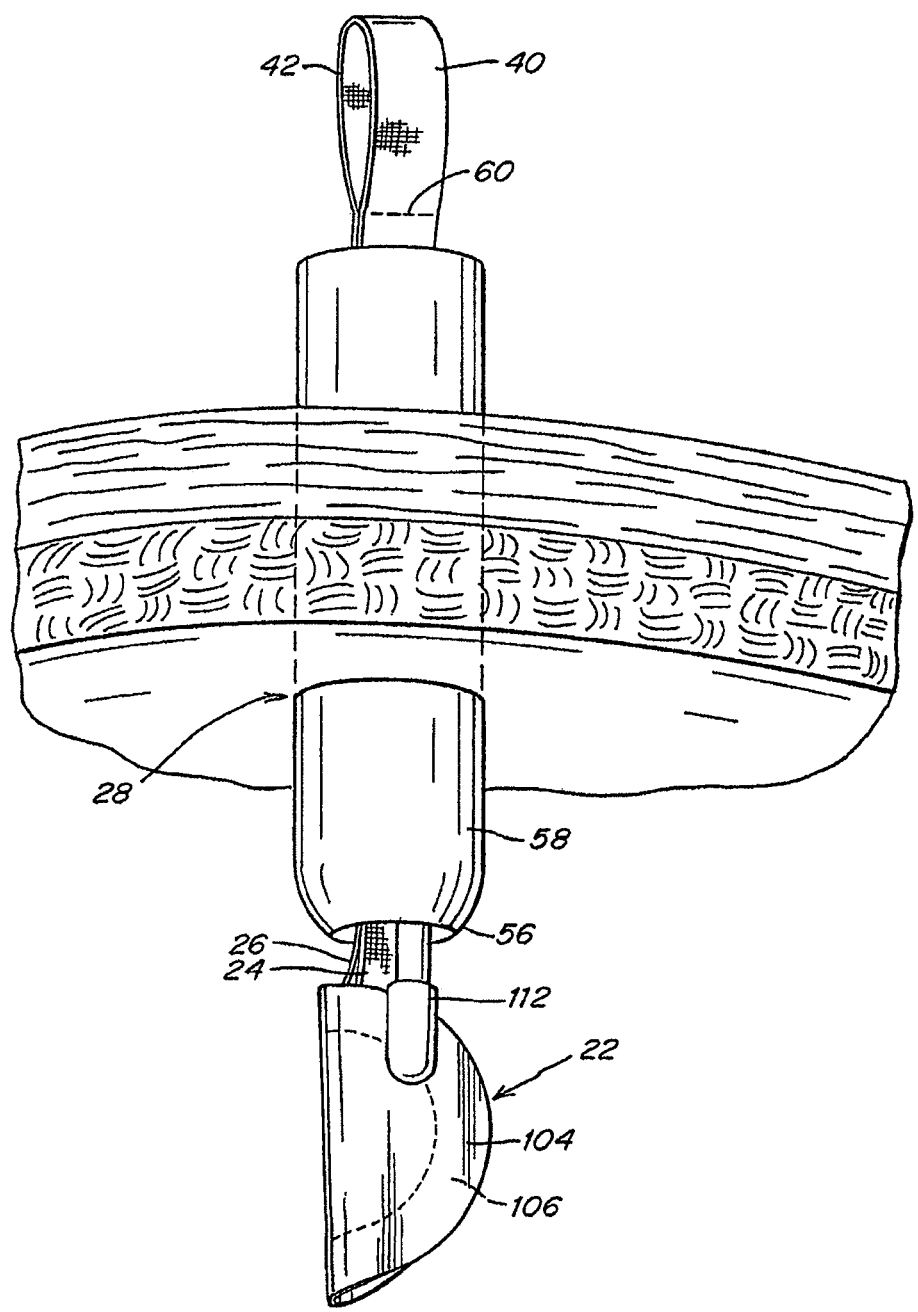
FIGS. 10-13 are schematic views illustrating repair of a trocar tract using the prosthesis of FIG. 2 in accordance with another illustrative embodiment of the invention.

To deliver the prosthesis to the defect site, the patch is folded in half to form a taco-like configuration and then held in the jaws of a grasper 112. The distal end of the grasper 112 is then advanced through and out of the cannula 58 and to the surgical site as shown in FIG. 10.

Figure 11:
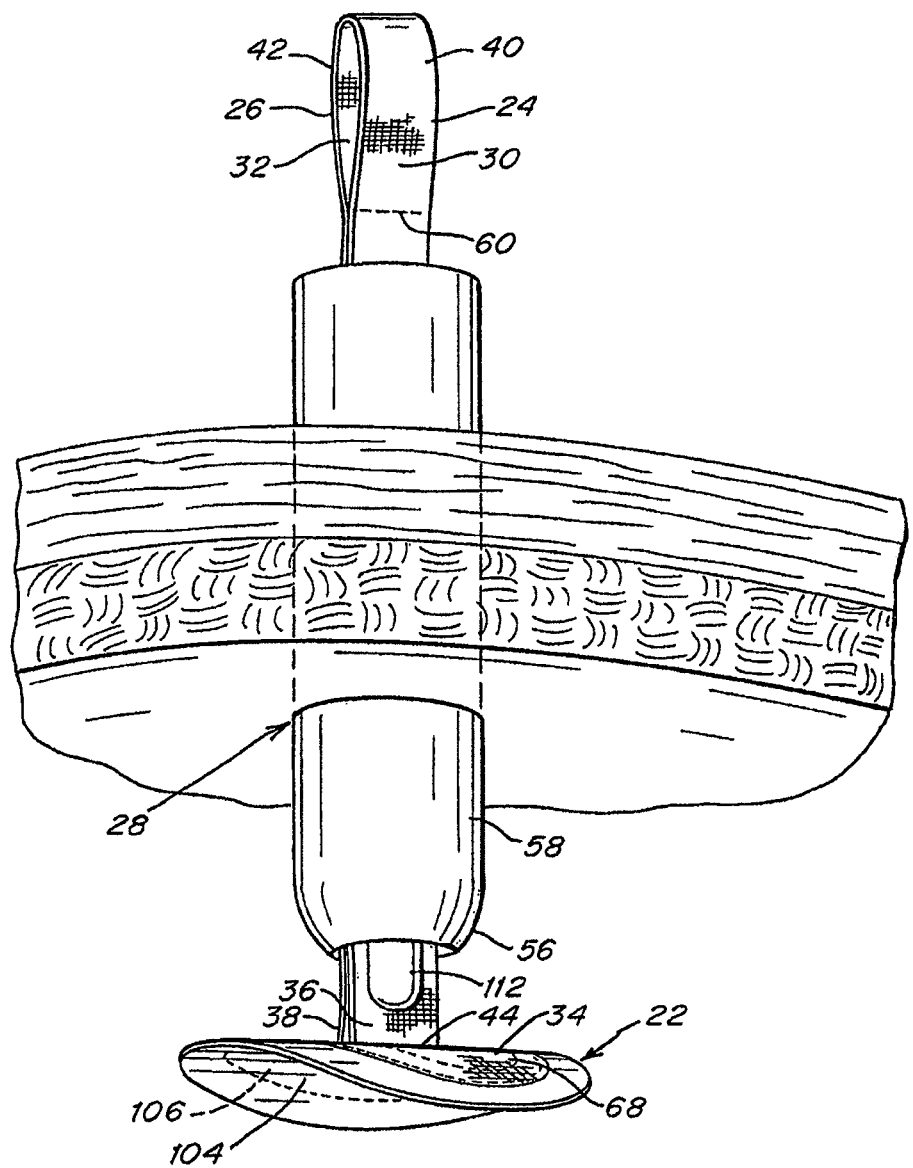
Figure 12:
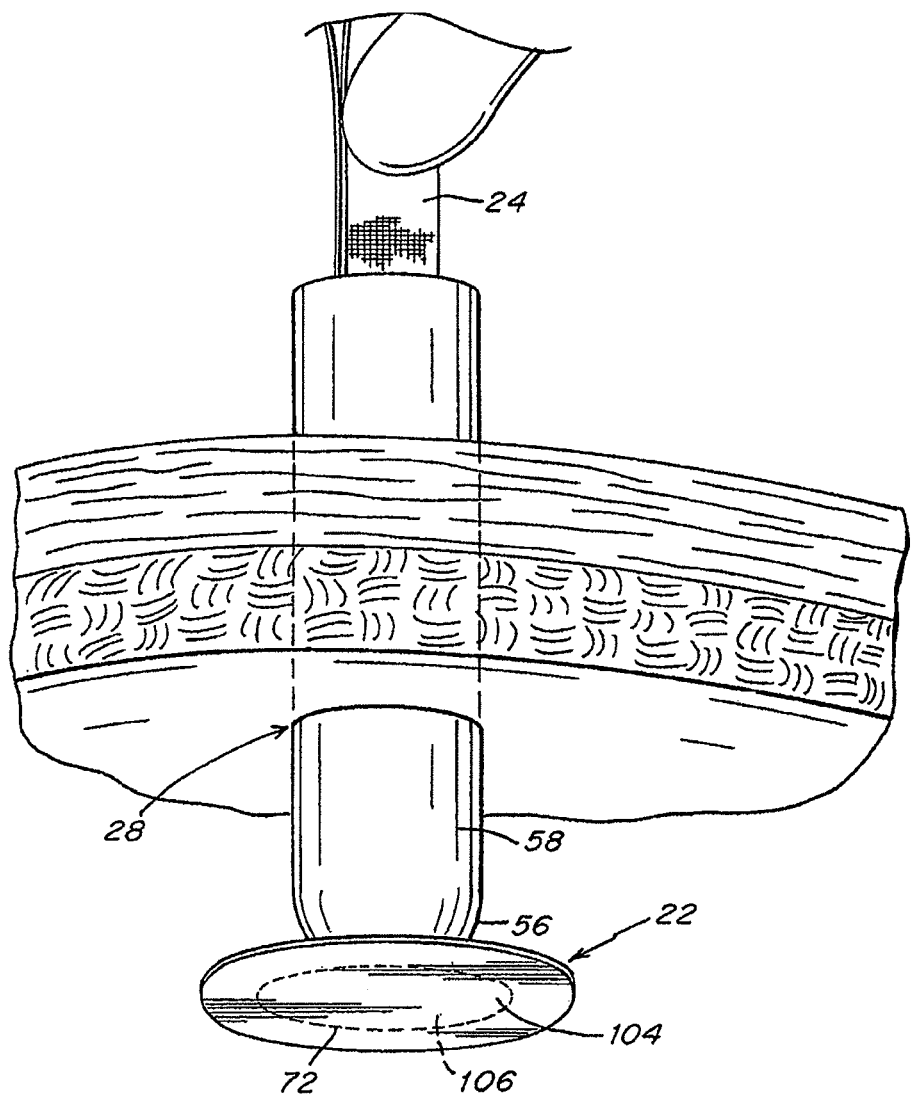

When the patch 22 is clear of the distal end side of the cannula 58, as indicated either by the location of the indicator 60 relative to the cannula, by the sensed change in feel of the grasper, or by visualization with a laparoscopic camera, the jaws of the grasper 112 are opened, releasing the folded patch 22. The resilient support member 98, no longer confined by the graspers, expands deploying the patch 22 into a substantially planar configuration as shown in FIG. 11. The free proximal ends of the tethers 24, 26 are then pulled away from the cannula, drawing the patch 22 up against the distal end 56 of the cannula 58 as shown in FIG. 12.

Figure 13:
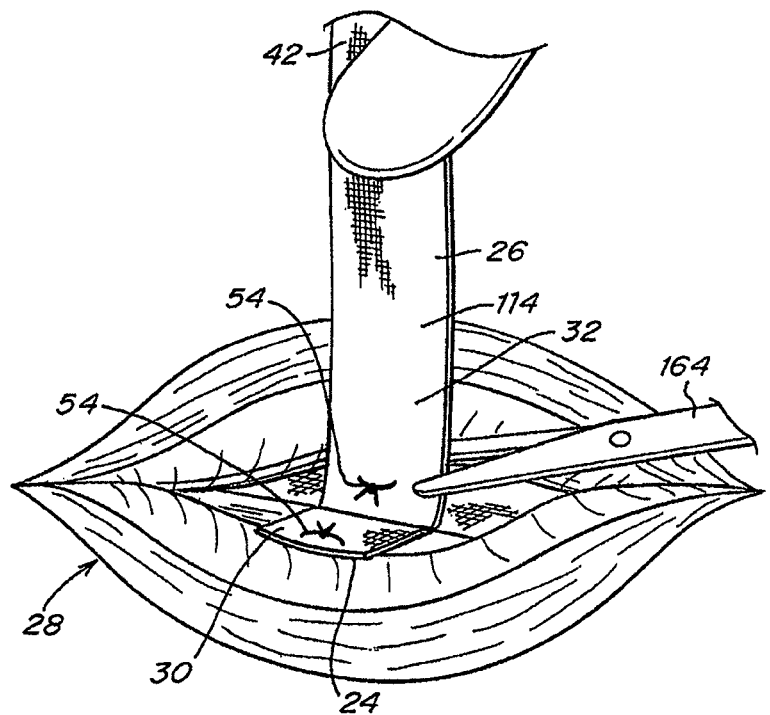

While maintaining tension on the tethers, the cannula is slowly removed from the defect, seating the patch against the defect. The tethers are then pulled away from each other, providing access to the pocket 78 in the patch. The physician may probe with her finger about the pocket to ensure proper deployment and placement of the patch over the defect. The tethers 24, 26 may then be attached to the tissue and muscle adjacent the defect as shown in FIG. 13. In the repair of a trocar wound in the abdominal cavity, the tethers may be attached with sutures 54 to the fascia or to the abdominal wall near the edge of the defect. Any excess tether length 114 may then be cut and discarded. The skin overlying the defect may then be closed by suturing or other conventional approach.

Figure 14:
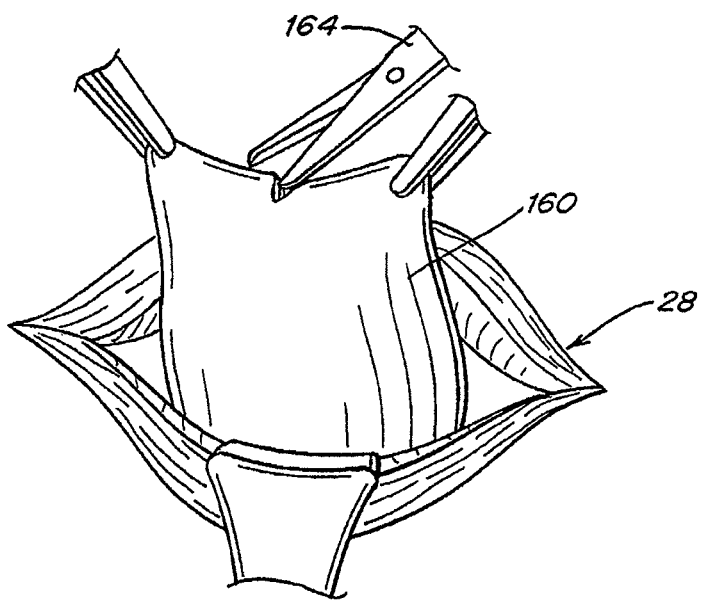
FIG. 14-16 are schematic views illustrating an umbilical hernia repair using the prosthesis of FIG. 2 in accordance with a further illustrative embodiment of the invention.
Figure 15:
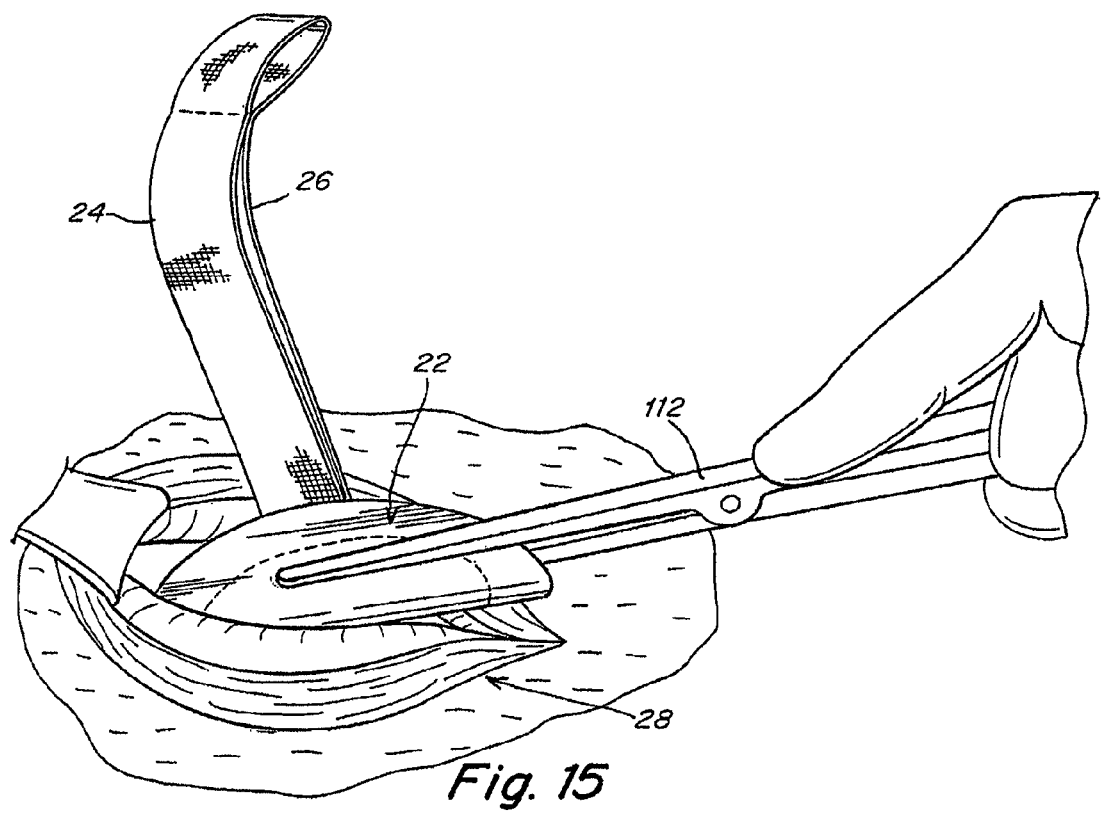
Figure 16:
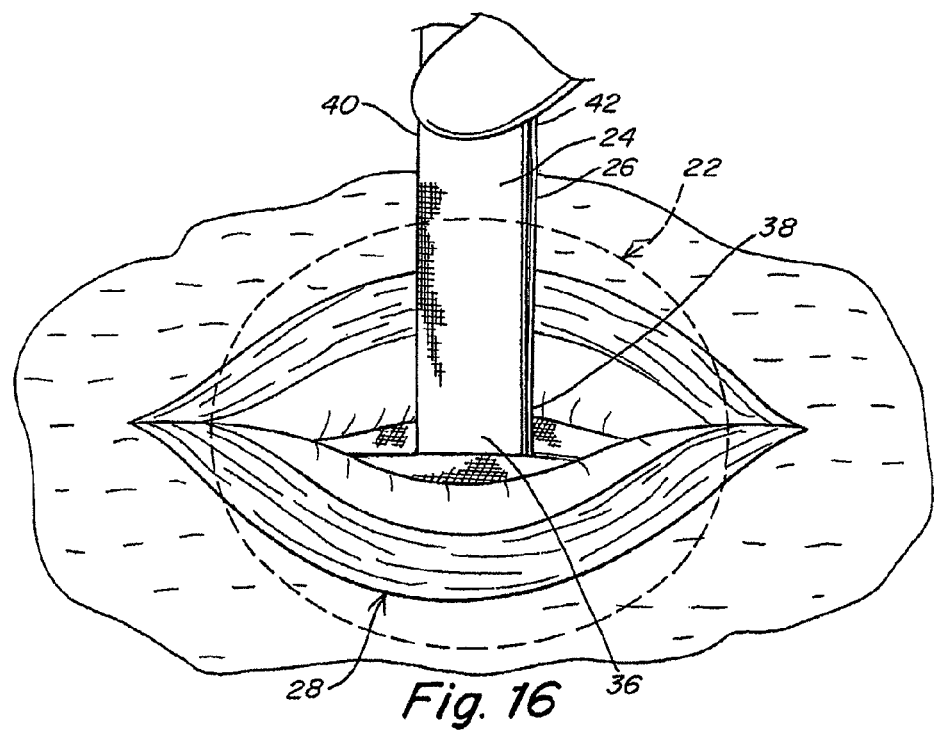

One embodiment of an umbilical hernia repair will now be described with reference to FIGS. 14-16. Upon identifying the defect 28, a small incision is made over the hernia. The hernia sac 160 may be dissected out and divided, as shown in FIG. 14, with a cutting instrument, such as a scissors 164 or scalpel. The contents of the hernia sac may then be reduced, and the sac 160 ligated. A finger or peanut sponge may be inserted into the defect 28 to clear off the underside of the peritoneum proximate the incision over the defect. To deliver the prosthesis to the defect site, the patch 22 is folded in half to form a taco-like configuration and then held in the jaws of the grasper 112, as shown in FIG. 15. The defect may be retracted and the distal end of the grasper 112 is then advanced through the defect and into the intra-abdominal space and to the surgical site.

When the patch 22 is cleared of the defect opening, such as may be indicated by the location of the indicator relative to a reference point, the jaws of the grasper 112 are opened, releasing the folded patch 22. The resilient support member 98 of the patch, no longer confined by the graspers, expands and deploys the patch 22 into a substantially planar configuration. The free proximal ends of the tethers 24, 26 are then pulled away from the wound, drawing the patch 22 against the abdominal wall, as shown in FIG. 16.

The physician may sweep circumferentially about the patch to make sure that the patch is lying flat and that there is nothing such as the bowel or omentum, caught between the patch and the abdominal wall. The tethers may then be pulled away from each other, providing access to the pocket 78 and the patch. The physician may probe with her finger about the pocket to ensure proper deployment and placement of the patch over the defect. Additionally, while pulling up on the positioning tethers, the physician may insert a finger or peanut sponge into the defect and in between the surface of the patch facing the defect and the peritoneum.

The tethers 24, 26 may then be attached to the tissue and muscle or other anatomy adjacent the defect, similarly as shown with reference to FIG. 13. In the repair of an umbilical hernia in the abdominal cavity, the tethers may be attached with sutures 54 to the fascia or to the abdominal wall near the edge of the defect. Any excess tether length 114 may then be cut and discarded. Skin overlying the defect may then be closed by suturing or other conventional approach.

It should be understood that the foregoing description of the invention is intended merely to be illustrative thereof and that other embodiments, modifications, and equivalents of the invention are within the scope of the invention recited in the claims appended hereto. Further, the prostheses described above include various features that may be employed singularly or in any suitable combination.

What is claimed:

1. An implantable prosthesis for repairing an abdominal wall defect, the implantable prosthesis comprising:
   a multi-layer soft tissue repair patch including a first mesh layer, a second mesh layer and an adhesion resistant barrier layer, the first mesh layer located between the second mesh layer and the barrier layer; and
   at least one tether extending from a side of the repair patch opposite the barrier layer, the tether including a mesh portion integrally formed with the second mesh layer, the tether having a sufficient length to extend from the patch and through the abdominal wall defect when the patch is on one side of the defect, so that a portion of the tether is accessible on the other side of the defect for manipulation from outside a patient's body.

2. The implantable prosthesis of claim 1, further comprising a support member to support the repair patch in an unfolded configuration.

3. The implantable prosthesis of claim 2, wherein the support member is disposed on the repair patch.

4. The implantable prosthesis of claim 2, wherein the at least one tether extends from the patch inward of the support member.

5. The implantable prosthesis of claim 2, wherein the repair patch includes an outer peripheral edge, the support member being located inward of the outer peripheral edge.

6. The implantable prosthesis of claim 1, wherein the barrier layer is absorbable.

7. The implantable prosthesis of claim 1, wherein the first mesh layer is non-absorbable.

8. The implantable prosthesis of claim 1, wherein the at least one tether includes a pair of tethers integrally formed with the second mesh layer.

9. The implantable prosthesis of claim 8, wherein the second mesh layer includes an opening extending therethrough, the opening being located between the pair of tethers.

10. The implantable prosthesis of claim 9, wherein each tether is located along a side of the opening.

11. The implantable prosthesis of claim 8, wherein the tethers are joined to form a handle that may be grasped and pulled.

12. An implantable prosthesis for repairing an abdominal wall defect, the implantable prosthesis comprising:
   a multi-layer soft tissue repair patch including a first mesh layer, a second mesh layer and an adhesion resistant barrier layer, the first mesh layer located between the second mesh layer and the barrier layer; and
   at least one tether extending from a side of the repair patch opposite the barrier layer, the tether having a width and a thickness with the width varying along a length thereof, the tether having a sufficient length to extend from the patch and through the abdominal wall defect when the patch is on one side of the defect, so that a portion of the tether is accessible on the other side of the defect for manipulation from outside a patient's body.

13. The implantable prosthesis of claim 12, wherein the tether includes first and second ends with the first end being joined to the repair patch, the tether being wider at the first end and narrower away from the first second end.

14. The implantable prosthesis of claim 12, further comprising a support member to support the repair patch in an unfolded configuration.

15. The implantable prosthesis of claim 14, wherein the support member is disposed on the repair patch.

16. The implantable prosthesis of claim 14, wherein the at least one tether extends from the patch inward of the support member.

17. The implantable prosthesis of claim 16, wherein the repair patch includes an outer peripheral edge, the support member located inward of the outer peripheral edge.

18. The implantable prosthesis of claim 12, wherein the barrier layer is absorbable.

19. The implantable prosthesis of claim 12, wherein the first mesh layer is non-absorbable.

20. The implantable prosthesis of claim 12, wherein the at least one tether includes a mesh material.

21. The implantable prosthesis of claim 20, wherein the at least one tether includes a portion of the second mesh layer.

22. The implantable prosthesis of claim 21, wherein the at least one tether includes a pair of tethers integrally formed with the second mesh layer.

23. The implantable prosthesis of claim 22, wherein the second mesh layer includes an opening extending therethrough, the opening being located between the pair of tethers.

24. The implantable prosthesis of claim 23, wherein each tether is located along a side of the opening.

25. The implantable prosthesis of claim 22, wherein the tethers are joined to form a handle that may be grasped and pulled.

26. The implantable prosthesis of claim 20, wherein the at least one tether includes a suture.

27. An implantable prosthesis for repairing an abdominal wall defect, the implantable prosthesis comprising:
   a multi-layer soft tissue repair patch including a first mesh layer, a second mesh layer and an absorbable barrier layer, the first mesh layer located between the second mesh layer and the barrier layer;
   a support member to support the repair patch in an unfolded configuration; and
   a pair of tethers extending from a side of the repair patch opposite the barrier layer and inward of the support member, each tether including a portion of mesh material that forms the second mesh layer, the tether having a sufficient length to extend from the patch and through the abdominal wall defect when the patch is on one side of the defect, so that a portion of the tether is accessible on the other side of the defect for manipulation from outside a patient's body.

28. The implantable prosthesis of claim 27, wherein the repair patch includes an outer peripheral edge, the support member being located inward of the outer peripheral edge.

29. The implantable prosthesis of claim 27, wherein the barrier layer minimizes tissue attachment to the patch.

30. The implantable prosthesis of claim 27, wherein the first mesh layer is non-absorbable.

31. The implantable prosthesis of claim 27, wherein the second mesh layer includes an opening extending therethrough, the opening being located between the pair of tethers.

32. The implantable prosthesis of claim 31, wherein each tether is located along a side of the opening.

33. The implantable prosthesis of claim 27, wherein the tethers are joined to form a handle that may be grasped and pulled.

34. The implantable prosthesis of claim 27, wherein the support member is disposed on the repair patch.

35. The implantable prosthesis of claim 27, wherein each tether includes a suture.

36. An implantable prosthesis for repairing an abdominal wall defect, the implantable prosthesis comprising:
   a multi-layer soft tissue repair patch including a first mesh layer, a second mesh layer and an adhesion resistant barrier layer, the first mesh layer located between the second mesh layer and the barrier layer, the second mesh layer having an opening therethrough;
   a support member to support the repair patch in an unfolded configuration; and
   a pair of tethers extending from a side of the repair patch opposite the barrier layer and inward of the support member, the tethers extending from spaced apart portions of the repair patch with the opening located therebetween, each tether having a sufficient length to extend from the patch and through the abdominal wall defect when the patch is on one side of the defect, so that a portion of the tether is accessible on the other side of the defect for manipulation from outside a patient's body.

37. The implantable prosthesis of claim 36, wherein the repair patch includes an outer peripheral edge, the support member being located inward of the outer peripheral edge.

38. The implantable prosthesis of claim 36, wherein the barrier layer is absorbable.

39. The implantable prosthesis of claim 36, wherein the first mesh layer is non-absorbable.

40. The implantable prosthesis of claim 36, wherein the opening extends across the width of the second layer.

41. The implantable prosthesis of claim 36, wherein each tether is located along a side of the opening.

42. The implantable prosthesis of claim 36, wherein the tethers are joined to form a handle that may be grasped and pulled.

43. The implantable prosthesis of claim 36, wherein each tether includes a mesh portion and a suture.

44. The implantable prosthesis of claim 36, wherein the support member is disposed on the repair patch.

45. An implantable prosthesis for repairing an abdominal wall defect, the implantable prosthesis comprising:
   a multi-layer soft tissue repair patch including a first mesh layer, a second mesh layer and an adhesion resistant barrier layer, the first mesh layer located between the second mesh layer and the barrier layer; and at least one tether extending from a side of the repair patch opposite the barrier layer, the tether including a mesh portion and a suture portion, the tether having a sufficient length to extend from the patch and through the abdominal wall defect when the patch is on one side of the defect, so that a portion of the tether is accessible on the other side of the defect for manipulation from outside a patient's body.

46. The implantable prosthesis of claim 45, further comprising a support member to support the repair patch in an unfolded configuration.

47. The implantable prosthesis of claim 46, wherein the support member is disposed on the repair patch.

48. The implantable prosthesis of claim 46, wherein the at least one tether extends from the patch inward of the support member.

49. The implantable prosthesis of claim 48, wherein the repair patch includes an outer peripheral edge, the support member being located inward of the outer peripheral edge.

50. The implantable prosthesis of claim 46, wherein the support member is disposed on the repair patch.

51. The implantable prosthesis of claim 45, wherein the barrier layer is absorbable.

52. The implantable prosthesis of claim 45, wherein the first mesh layer is non-absorbable.

53. The implantable prosthesis of claim 45, wherein the at least one tether includes a pair of tethers.

54. The implantable prosthesis of claim 53, wherein the second mesh layer includes an opening extending therethrough, the opening being located between the pair of tethers.

55. The implantable prosthesis of claim 54, wherein each tether is located along a side of the opening.

56. The implantable prosthesis of claim 53, wherein the tethers are joined to form a handle that may be grasped and pulled.

* * * * *